United States Patent
Rolfs et al.

(10) Patent No.: US 11,092,609 B2
(45) Date of Patent: Aug. 17, 2021

(54) METHOD FOR THE DIAGNOSIS OF GAUCHER'S DISEASE

(71) Applicant: Centogene GmbH, Rostock (DE)

(72) Inventors: Arndt Rolfs, Berlin (DE); Hermann Mascher, Traiskirchen (AT)

(73) Assignee: Centogene GmbH, Rostock (DE)

( * ) Notice: Subject to any disclaimer, the term of this patent is extended or adjusted under 35 U.S.C. 154(b) by 482 days.

(21) Appl. No.: 15/966,734

(22) Filed: Apr. 30, 2018

(65) Prior Publication Data

US 2018/0259538 A1 Sep. 13, 2018

Related U.S. Application Data

(62) Division of application No. 14/124,375, filed as application No. PCT/EP2012/002409 on Jun. 6, 2012, now Pat. No. 10,859,580.

(30) Foreign Application Priority Data

Jun. 6, 2011 (EP) .................................. 11004597

(51) Int. Cl.
*G01N 33/68* (2006.01)
*G01N 33/92* (2006.01)
*C12N 9/42* (2006.01)

(52) U.S. Cl.
CPC ......... *G01N 33/6893* (2013.01); *G01N 33/92* (2013.01); *C12N 9/2442* (2013.01); *G01N 2405/10* (2013.01); *G01N 2800/044* (2013.01)

(58) Field of Classification Search
CPC .... G01N 33/50; G01N 33/6893; G01N 33/92; G01N 2405/10; G01N 2800/044
See application file for complete search history.

(56) References Cited

U.S. PATENT DOCUMENTS

| | | | |
|---|---|---|---|
| 5,236,838 A * | 8/1993 | Rasmussen | C12N 15/85 435/209 |
| 7,528,153 B2 | 5/2009 | Aerts | |
| 7,829,579 B2 | 11/2010 | Wustman | |
| 2010/0266571 A1 | 10/2010 | Lockhart et al. | |

FOREIGN PATENT DOCUMENTS

| | | |
|---|---|---|
| EP | 2154969 | 2/2010 |
| JP | 2010-523715 A | 7/2015 |
| WO | 2006133446 A2 | 12/2006 |
| WO | 2008/128106 A | 10/2008 |
| WO | WO2008/134628 | 11/2008 |

OTHER PUBLICATIONS

Cabrera-Salazar et al. (Experimental Neurology, 2010, 225:436-444) (Year: 2010).*

(Continued)

*Primary Examiner* — Jeremy C Flinders
(74) *Attorney, Agent, or Firm* — Stanek Lemon Crouse & Meeks, PA

(57) ABSTRACT

The present invention is related to an in vitro method for diagnosing Gaucher's disease in a subject comprising a step of
a) detecting a biomarker in a sample from the subject, wherein the biomarker is free lyso-Gb1.

8 Claims, 12 Drawing Sheets

(56) References Cited

OTHER PUBLICATIONS

Enquist et al. (Proc. Natl. Acad. Sci., 2007, 104(44): 17483-17488) (Year: 2007).*
Aerts et al., "Biomarkers in the diagnosis of lysosomal storage disorders: proteins, lipids, and inhibodies," J Inherit Metab Dis, Jun. 2011, 34(3), pp. 605-619, published online on Mar. 29, 2011.
Bodennec et al., "Simultaneous quantification of lyso-neutral glycosphingolipids and neutral glycosphingolipids by N-acetylation with [$^3$H]acetic anhydride," Journal of Lipid Research, vol. 44, May 2003, pp. 1415-1419.
Meikle et al., "Plasma lipids are altered in Gaucher disease: Biochemical markers to evaluate therapeutic intervention," Blood Cells Mol Dis., May-Jun. 2008, 40(3), pp. 420-427.
Mistry et al., "Glucocerebrosidase gene-deficient mouse recapitulates Gaucher disease displaying cellular and molecular dysregulation beyond the macrophage," PNAS, Nov. 9, 2010, vol. 107, N45, pp. 19473-19478.
Mistry, P. K., "Introduction of Circulating and Other Biomarkers," Workshop, Sep. 20, 2010, 33 pages.
Mistry, P.K., Gaucher Disease Biomarker Qualification Workshop—Agenda, Sep. 20, 2010, "Introduction of Circulating and Other Biomarkers," 2 pages.
Muregesan et al, "Glucosylsphingosine is a key biomarker of Gaucher disease," American Journal of Hematology, vol. 91, N11, Nov. 2016, pp. 1082-1089.
Rolfs et al., "Glucosylsphingosine Is a Highly Sensitive and Specific Biomarker for Primary Diagnostic and Follow-Up Monitoring in Gaucher Disease in a Non-Jewish, Caucasian Cohort of Gaucher Disease Patients," PLOS ONE, Nov. 2013, vol. 8, Issue 11, pp. 1-9.
Togawa et al., "Plasma globotriaosylsphingosine as a biomarker of Fabry disease," Mol Gen. and Metabolism 100, 2010, pp. 257-261.
Vissers et al., "Analysis and quantification of diagnostic serum markers and protein signatures for Gaucher Disease," Molecular & Cellular Proteomics 6.5, 2007, pp. 755-766.
Chace, et al., "Use of Tandem Mass Spectrometry for Multianalyte Screening of Dried Blood Specimens from Newborns," Clinical Chemistry 49:11, 2003, p. 1797-1817.
Nakamura et al., "Newborn Screening for Lysosomal Storage Disorders," American Journal of Medical Genetics Part C (Seminars in Medical Genetics, 157, 2011, pp. 63-71.
Nilsson et al., "Increased cerebroside concentration in plasma and erythrocytes in Gaucher disease: significant differences between type I and type III.", Clin. Genel., Nov. 1982, 22 (5), Abstract.
Third Party Submission mailed Jan. 11, 2016 for a corresponding European application No. 12728976.7.
Dekker N et al., "Elevated plasma glucosylsphingosine in Gaucher disease: relation to phenotype, storage cell markers, and therapeutic response", blood-2011-05-352971. Epub Aug. 25, 2011.
Matreya LLC., Glucosylsphingosine, retrieved on Dec. 23, 2015.
Orvisky E et al., "Glucosylsphingosine accumulation in tissues from patients with Gaucher disease: correlation with phenotype and genotype", Mol Genet Metab. Aug. 2002; 76(4):262-70.
Orvisky E et al., "Glucosylsphingosine accumulation in mice and patients with type 2 Gaucher disease begins early in gestation", Pediatr Res. Aug. 2000; 48(2):233-7.
Schueler U.H. et al., "Toxicity of glucosylsphingosine (glucopsychosine) to cultured neuronal cells: a model system for assessing neuronal damage in Gaucher disease type 2 and 3", Neurobiol Dis. Dec. 2003; 14(3):595-601.
Ying Sun et al., Neuronopathic Gaucher disease in the mouse: viable combined selective saposin C deficiency and mutant glucocerebrosidase (V394L) mice with glucosylsphingosine and glucosylceramide accumulation and progressive neurological deficits, Human Molecular Genetics, 2010, vol. 19, No. 6, p. 1088-1097.
Japanese Office Action dated Mar. 31, 2016 for a corresponding Japanese application No. 2004-513942.
Turgeon et al., "Measurement of psychosine in dried blood spots—a possible improvement to newborn screening programs for Krabbe disease", J Inherit Metab Dis 38: 923-929, Sep. 2015.
Chinese Office Action dated Dec. 2, 2015 issued to a corresponding Chinese patent application No. 201280027860.3.
Kevin Mills et al., "The synthesis of internal standards for the quantitative determination of sphingolipids by tandem mass spectrometry", Rapid Commun. Mass Spectrom., vol. 19, No. 12, pp. 1739-1748, May 23, 2005.
Benistan, et al. "Prenatal diagnosis of Gaucher disease," la revue de medicine interne 28: S193-S197 (2007).
International Preliminary Report on Patentability for International Application PCT/EP2012/002409, dated Dec. 10, 2013.
Auray-Blais, et al.: "How well does urinary lyso-Gb3 function as a biomarker in Fabry disease?", Clinical Chimica Acta, Elsevier BV. (411)23-24: 1906-1914 (2010).
International Search Report for International Application PCT/EP2012/002409, dated Jul. 20, 2012.
Orvisky et al. (2002) "Glucosylsphingosine accumulation in tissues from patients with Gaucher disease: correlation with phenotype and genotype" Molecular Genetics and Metabolism 76(4):262-270.
Boot et al. (2004) "Marked elevation of the chemokine CCL18/PARC in Gaucher disease: a novel surrogate marker for assessing therapeutic intervention" Blood 103(1):33-39.
Oshima (1976) "Identification of glucosyl sphingosine from Gaucher's spleen by gas chromatography-electron impact and GC-chemical ionization mass spectrometry." J Biochem 80(1):53-59.
Groener et al. (2008) "Plasma glucosylceramide and ceramide in type 1 Gaucher disease patients: Correlations with disease severity and response to therapeutic intervention" Biochimica et Biophysica Acta 1781(1-2):72-78.

* cited by examiner

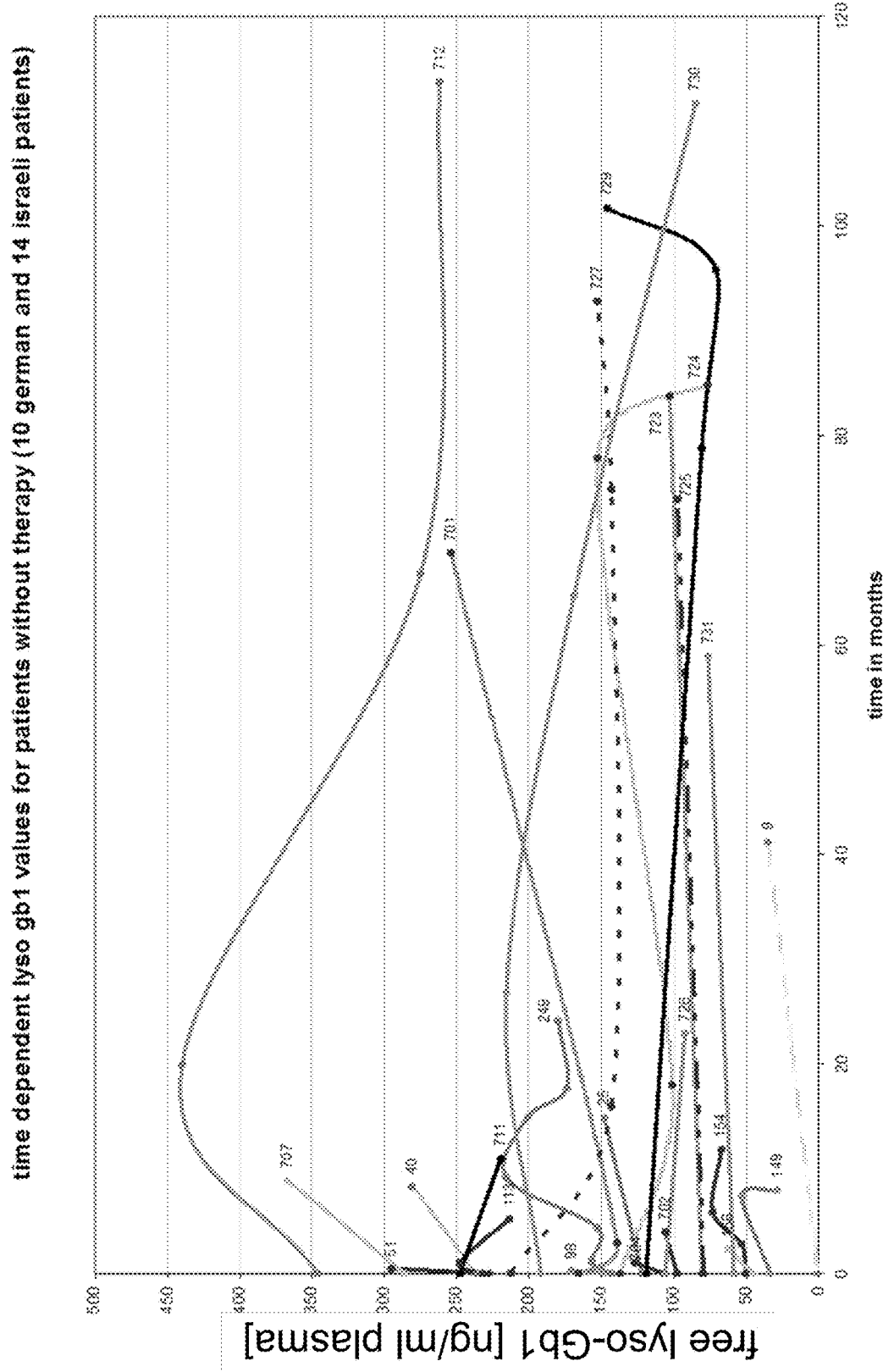

Fig. 4

| Amino acid | homozygous | Compound heterozygous |
|---|---|---|
| Patients tested having mutation N370S | 3 | 48 |
| median (IQR) free lyso gb1 (first value before therapy) | 159 ng/ml | 45.4 (16.7-114.8) ng/ml |
| Patients tested having mutation L444P | 9 | 15 |
| median (IQR) free lyso gb1 (first value before therapy) | 194 (89.4-364.5) ng/ml | 89 (41.2-117) ng/ml |

METHOD FOR THE DIAGNOSIS OF GAUCHER'S DISEASE

CROSS-REFERENCE TO RELATED APPLICATIONS

The present application is a divisional of U.S. patent application Ser. No. 14/124,375, filed Mar. 13, 2014, which is a U.S.C. § 371 national phase application of PCT International Application No. PCT/EP2012/002409, filed Jun. 6, 2012, which claims priority to European Patent Application No. 11004597.8, filed Jun. 6, 2011. The disclosures of each are hereby incorporated herein by reference in their entireties.

FIELD OF THE INVENTION

The present invention is related to a method for diagnosing Gaucher's disease in a subject, a method for determining the course of Gaucher's disease in a subject, a method for determining the effectiveness of at least one treatment applied to a subject being positively tested for suffering from or being at risk for developing Gaucher's disease, a method of determining the effectiveness of a compound for the treatment of Gaucher's disease, use of mass spectrometry for the detection of a biomarker, use of a biomarker for Gaucher's disease, a kit for determining the presence of a biomarker in a sample from a subject and a software product, wherein the biomarker is free lyso-Gb1.

BACKGROUND OF THE INVENTION

Lysosomal storage diseases, also referred to herein as lysosomal storage disorders or LSDs, are a group of rare inherited metabolic disorders that result from defects in lysosomal function. LSDs result when a specific organelle in the body's cells—the lysosome—malfunctions. Some of the more prominent lysosomal storage diseases are Gaucher's disease and Fabry disease.

LSDs are caused by lysosomal dysfunction usually as a consequence of deficiency of a single enzyme required for the metabolism of lipids, glycoproteins or so-called mucopolysaccharides. Individually, LSDs occur with frequencies of about 1:10,000 to 1:250,000, however, as a group the incidence is about 1:5,000. Most of these disorders are autosomal recessively inherited; however, a few are X-linked inherited, such as Fabry disease and Hunter syndrome (MPS II).

Like other genetic diseases, individuals typically inherit lysosomal storage diseases from their parents. Although each disorder results from different gene mutations that translate into a deficiency in enzyme activity, they all share a common biochemical characteristic—nearly all lysosomal disorders originate from an abnormal accumulation of substances inside the lysosome.

Lysosomal storage diseases affect mostly children and they often die at a young and unpredictable age, many within a few months or years of birth. Many other children die of this disease following years of suffering from various symptoms of their particular disorder.

The symptoms of lysosomal storage disease vary, depending on the particular disorder and other variables like the age of onset, and can be mild to severe. They can include developmental delay, movement disorders, seizures, dementia, deafness and/or blindness. Some people with Lysosomal storage disease have enlarged livers (hepatomegaly) and enlarged spleens (splenomegaly), pulmonary and cardiac problems, and bones that develop abnormally.

There are no causative cures for lysosomal storage diseases and treatment is mostly symptomatic, although bone marrow transplantation and enzyme replacement therapy (ERT) have been used for some indications with good success. In addition, umbilical cord blood transplantation is being performed at specialized centers for a number of these diseases. In addition, substrate reduction therapy (SRT), a method used to decrease the accumulation of storage material, is currently being evaluated for some of these diseases. Furthermore, chaperone therapy, a technique used to stabilize the defective enzymes produced by patients, is being examined for certain of these disorders. Gene therapy constitutes a further option for the treatment of these diseases.

To date a definitive diagnosis of Gaucher's disease can only be made applying biochemical testing measuring directly the defect of the beta-glucosidase enzyme together with genetic confirmation. Since numerous different mutations may be the cause of a particular lysosomal storage disease the sequencing of the entire beta-glucosidase gene is applied in Gaucher's disease in order to confirm the diagnosis.

Although there are attempts to apply diagnosis methods based on associated biochemical abnormalities such as high alkaline phosphatase, angiotensin-converting enzyme (ACE) and immunoglobulin levels, or, in case of Gaucher's disease, by cell analysis showing "crinkled paper" cytoplasm and glycolipid-laden macrophages, there is an unmet need for a simple biochemical test exhibiting highly specific and highly sensitive detection of said lysosomal storage disease at an early stage, monitoring progression of the disease and early monitoring the efficacy of applied therapies.

Therefore, the identification of biomarkers for the early detection and diagnosis of Gaucher's diseases holds great promise to improve the clinical outcome of patients. It is especially important for patients with vague or no symptoms or to detect patients which fail to respond to a therapy.

A biomarker should be technically feasible in many hands, easy to measure; useful, with a consistent, relative magnitude between experimentals/patients and controls, or treated and untreated; reliable, precise, and accurate clinically, and classifiable as strongly predictive or prognostic.

In Gaucher's disease some lysosomal enzymes, used as indirect biomarkers, were found to be elevated, including tartrate-resistant acid phosphatase, hexosaminidase, and a human chitinase, chitotriosidase. Thus there are attempts to monitor the reduction of storage cells in tissues by measurement of such surrogate markers of Gaucher cells like chitotriosidase and CCL18 (C. E. Hollak et al. Marked elevation of plasma chitotriosidase activity. A novel hallmark of Gaucher disease, J. Clin. Invest. 93 (1994) 1288-1292; R. G. Boot et al. Marked elevation of the chemokine CCL18/PARC in Gaucher disease: a novel surrogate marker for assessing therapeutic intervention, Blood 103 (2004) 33-39). However, beside other disadvantages in the use of chitotriosidase as a biomarker for Gaucher's disease, said enzyme accumulates independent of a direct link to the pathology of Gaucher's disease. Furthermore, up to 35% of given ethnicities demonstrate a defect of the gene coding for chitotriosidase resulting in an artificially reduced or non-measurable chitotriosidase activity.

The use of primary storage molecules as biomarker was assessed for glucosyl ceramide (Gb1) in plasma of Gaucher's disease patients and compared to the level of Gb1 in healthy individuals (Groener et al. Biochim Biophys Acta.

2008 January-February; 1781(1-2):72-8. Epub 2007 Dec. 5.; Plasma glucosylceramide and ceramide in type 1 Gaucher disease patients: correlations with disease severity and response to therapeutic intervention.; Groener J E et al.). Nevertheless, although Gb1 measured in said study was increased in plasma of said patients, said increase of Gb1 was not prominent and thus the specificity and the sensitivity of the method were low showing that Gb1 is not applicable as a biomarker for Gaucher's disease.

Already in 1989 Rosengren et al. (Lysosulfatide (galactosylsphingosine-3-O-sulfate) from metachromatic leukodystrophy and normal human brain, Rosengren B, Fredman P, Månsson J E, Svennerholm L.; J Neurochem. 1989 April; 52(4):1035-41.) showed that in lipidoses not only the catabolism of the major sphingolipid but also its lyso-compound is affected. Nevertheless, said study concluded that the lyso-compounds do not play a key-role in the pathogenetic mechanisms in the sphingolipidoses. Thus, said lyso-compounds might not be suitable biomarkers for diagnosis of sphingolipidoses such as Gaucher's disease.

It is important to note that until today no use of a highly specific and highly sensitive biomarker and no method for the diagnosis of Gaucher's disease is available beside the methods described above, that exhibit an unsatisfactory limit of detection, sensitivity and/or specificity and thus proved to be unsuitable for clinical application.

Accordingly, there is need for a fast, simple and more importantly reliable method for the diagnosis of Gaucher's disease.

In the light of the above, the problem underlying the present invention is to provide a method for the diagnosis of Gaucher's disease.

A further problem underlying the present invention is to provide a method for determining the course and prognosis of Gaucher's disease.

A still further problem underlying the present invention is to provide a method for determining rather quickly the effectiveness of at least one treatment applied to a subject being positively tested for suffering from or being at risk of developing Gaucher's disease.

A further problem underlying the present invention is to provide a method for determining the effectiveness of a compound for the treatment of a Gaucher's disease.

Another problem underlying the present invention is to provide a biomarker which allows the specific and sensitive diagnosis of Gaucher's disease. A still further problem underlying the present invention is a kit which comprises a compound which interacts with a biomarker which is specific and sensitive for Gaucher's disease.

These and other problems are solved by the subject matter of the attached independent claims. Preferred embodiments may be taken from the dependent claims.

The problem underlying the present invention is solved in a first aspect which is also the first embodiment of the first aspect, by a method for diagnosing Gaucher's disease in a subject comprising a step of
  a) detecting a biomarker in a sample from the subject, wherein the biomarker is free lyso-Gb1.

In a second embodiment of the first aspect which is also an embodiment of the first embodiment of the first aspect, the method further comprises a step of
  b) determining a level of the biomarker present in the sample.

In a third embodiment of the first aspect which is also an embodiment of the first and the second embodiment of the first aspect, the level of the biomarker is indicative whether the subject is suffering from or whether the subject is at risk for developing Gaucher's disease.

In a fourth embodiment of the first aspect which is also an embodiment of the first, the second and the third embodiment of the first aspect, the sample from the subject is a sample from a subject who has been previously treated or diagnosed for Gaucher's disease.

In a fifth embodiment of the first aspect which is also an embodiment of the first, the second and the third embodiment of the first aspect, the sample from the subject is a sample from a subject who has not been previously treated or a subject who has not been previously diagnosed for Gaucher's disease.

In a sixth embodiment of the first aspect which is also an embodiment of the first, the second, the third, the fourth and the fifth embodiment of the first aspect, the method further comprises a step of
  c) applying, maintaining, reducing, elevating or not applying a therapy based on the diagnosis of whether the subject is suffering from or for being at risk for developing Gaucher's disease.

In a seventh embodiment of the first aspect which is also an embodiment of the first, the second, the third, the fourth, the fifth and the sixth embodiment of the first aspect, the method further comprises a step of
  d) detecting the biomarker in a sample from the subject after applying, maintaining, reducing, elevating or not applying a therapy in a step of c).

In an eighth embodiment of the first aspect which is also an embodiment of the first, the second, the third, the fourth, the fifth, the sixth and the seventh embodiment of the first aspect, the method further comprises a step of
  e) determining a level of the biomarker in the sample from the subject after applying, maintaining, reducing, elevating or not applying a therapy in a step of c).

In a ninth embodiment of the first aspect which is also an embodiment of the eighth embodiment of the first aspect, the method further comprises the step of
  f) determining whether the level of the biomarker determined in step b) is lower than the level of the biomarker determined in step e).

In a tenth embodiment of the first aspect which is also an embodiment of the ninth embodiment of the first aspect, the method further comprises the step of
  g) applying, maintaining, reducing, elevating or not applying a therapy based on the step of f).

In an eleventh embodiment of the first aspect which is also an embodiment of the first, the second, the third, the fourth, the fifth, the sixth, the seventh, the eighth, the ninth and the tenth embodiment of the first aspect, the method further comprises detecting at least one additional biomarker in the sample from the subject.

In a twelfth embodiment of the first aspect which is also an embodiment of the eleventh embodiment of the first aspect, the method further comprises determining the level of the at least one additional biomarker in the sample from the subject.

In a thirteenth embodiment of the first aspect which is also an embodiment of the eleventh and the twelfth embodiment of the first aspect, the at least one additional biomarker is selected from the group comprising chitotriosidase and CCL18.

In a fourteenth embodiment of the first aspect which is also an embodiment of the thirteenth embodiment of the first aspect, the at least one additional biomarker is chitotriosidase.

In a fifteenth embodiment of the first aspect which is also an embodiment of the thirteenth embodiment of the first aspect, the at least one additional biomarker is CCL18.

In a sixteenth embodiment of the first aspect which is also an embodiment of the first, the second, the third, the fourth, the fifth, the sixth, the seventh, the eighth, the ninth, the tenth, the eleventh, the twelfth, the thirteenth, the fourteenth and the fifteenth embodiment of the first aspect, the method further comprises detecting chitotriosidase and CCL18.

In a seventeenth embodiment of the first aspect which is also an embodiment of the first, the second, the third, the fourth, the fifth, the sixth, the seventh, the eighth, the ninth, the tenth, the eleventh, the twelfth, the thirteenth, the fourteenth, the fifteenth and the sixteenth embodiment of the first aspect, the biomarker and/or the at least one additional biomarker is detected by means of immunoassay, mass spectrometric analysis, biochip array, functional nucleic acids and/or a fluorescent derivative of free lyso-Gb1.

In an eighteenth embodiment of the first aspect which is also an embodiment of the seventeenth embodiment of the first aspect, the biomarker is detected by means of mass spectrometric analysis.

In a nineteenth embodiment of the first aspect which is also an embodiment of the eighteenth embodiment of the first aspect, mass spectrometric analysis is selected from the group consisting of SELDI, MALDI, MALDI-Q TOF, MS/MS, TOF-TOF and ESI-O-TOF.

In a twentieth embodiment of the first aspect which is also an embodiment of the nineteenth embodiment of the first aspect, the mass spectrometric analysis uses MS/MS.

In a twenty first embodiment of the first aspect which is also an embodiment of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth and the twentieth embodiment of the first aspect, the method further comprises protein precipitation and/or HPLC.

In a twenty second embodiment of the first aspect which is also an embodiment of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth and the twenty first embodiment of the first aspect, the method further comprises protein precipitation, HPLC and MS/MS.

In a twenty third embodiment of the first aspect which is also an embodiment of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty first and the twenty second embodiment of the first aspect, the subject is a human.

In a twenty fourth embodiment of the first aspect which is also an embodiment of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty first, the twenty second and the twenty third embodiment of the first aspect, the step of detecting the biomarker in a sample comprises subjecting the sample to a protein precipitation step, precipitating protein from the sample, wherein precipitating protein from the sample provides a supernatant of the sample, subjecting the supernatant of the sample to HPLC and MS/MS and determining the amount of the biomarker and/or the at least one additional biomarker that is/are present in the supernatant of the sample.

The problem underlying the present invention is solved in a second aspect which is also the first embodiment of the second aspect, by a method for diagnosing Gaucher's disease in a subject comprising
i) adding an internal standard to a sample from the subject, wherein the sample form the subject is selected from the group comprising plasma, serum and blood;
ii) optionally mixing the sample containing the internal standard;
iii) subjecting the sample to a protein precipitation step, whereby protein from the sample is precipitated and a supernatant of the sample is provided;
iv) optionally subjecting the supernatant of the sample to a first separation step which provides a supernatant, whereby preferably the first separation step is a step of centrifugation;
v) subjecting the supernatant of step c) or of step d), or a part thereof, to a second separation step, wherein the second separation step comprises injecting a part of the supernatant into an HPLC-MS/MS system and using an HPLC column with a gradient form acidic water to acetonitrile/acetone; wherein the HPLC column is preferably an HPLC column selected from the group comprising C8 and C18 HPLC column, and wherein the second separation step provides a separated sample;
vi) subjecting the separated sample to MS/MS, wherein MS/MS comprises electrospray ionization and Multiple Reacting Monitoring;
wherein the method is preferably a method according to any one of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty first, the twenty second, the twenty third and the twenty-fourth embodiment of the first aspect;
and further comprising a step of
  a) detecting a biomarker in a sample from the subject, wherein the biomarker is free lyso-Gb1;
and optionally a step of
  b) determining a level of the biomarker present in the sample.

In a second embodiment of the second aspect which is also an embodiment of the first embodiment of the second aspect, the internal standard comprises D5-fluticasone propionate and/or lyso-Gb2.

In a third embodiment of the second aspect which is also an embodiment of the first and the second embodiment of the second aspect and of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty first, the twenty second, the twenty third and the twenty fourth embodiment of the first aspect, the step of b) and/or the step of e) further comprises that the level of the biomarker in the sample from the subject is compared to a cut-off level.

In a fourth embodiment of the second aspect which is also an embodiment of the first, the second and the third embodiment of the second aspect and of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty first, the twenty second, the twenty third and the twenty fourth embodiment of the first aspect, preferably of the third embodiment of the second aspect, a level of the biomarker in the sample from the subject which is higher than the cut-off level is indicative that the subject is suffering from or is at risk for developing Gaucher's disease.

In a fifth embodiment of the second aspect which is also an embodiment of the fourth embodiment of the second aspect, a level of the biomarker in the sample from the subject which is lower than the cut-off level is indicative that the subject is not suffering from or is not at risk for developing Gaucher's disease.

In a sixth embodiment of the second aspect which is also an embodiment of the first, the second, the third, the fourth and the fifth embodiment of the second aspect and of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third and the twenty-fourth embodiment of the first aspect, the cut-off level is selected such that a sensitivity for diagnosing Gaucher's disease in a subject is preferably from about 98.5% to 100%, more preferably 100% and that a specificity for diagnosing Gaucher's disease in a subject is preferably from 99.4% to 100%, more preferably 100%.

In a seventh embodiment of the second aspect which is also an embodiment of the first, the second, the third, the fourth, the fifth and the sixth embodiment of the second aspect and of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third and the twenty-fourth embodiment of the first aspect, the step of b) and/or the step of e) further comprises that a level of the biomarker in said subject is compared to a level of the biomarker detected in a sample from a control.

In an eighth embodiment of the second aspect which is also an embodiment of the seventh embodiment of the second aspect, the control is a sample from a subject being positively tested for not having Gaucher's disease.

In a ninth embodiment of the second aspect which is also an embodiment of the first, the second, the third, the fourth, the fifth, the sixth, the seventh and the eighth embodiment of the second aspect and of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third and the twenty-fourth embodiment of the first aspect, a level of the biomarker in the sample from the subject which is higher than a level of the biomarker in the control sample is indicative that the subject is suffering from and/or is at risk for developing Gaucher's disease.

In a tenth embodiment of the second aspect which is also an embodiment of the first, the second, the third, the fourth, the fifth, the sixth, the seventh, the eighth and the ninth embodiment of the second aspect and of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third and the twenty-fourth embodiment of the first aspect, Gaucher's disease is selected from the group comprising the non-neuronopathic type I, the chronic neuronopathic type II and the acute neuronopathic type III.

In an eleventh embodiment of the second aspect which is also an embodiment of the first, the second, the third, the fourth, the fifth, the sixth, the seventh, the eighth, the ninth and the tenth embodiment of the second aspect and of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third and the twenty-fourth embodiment of the first aspect, preferably of the tenth embodiment of the second aspect, the sample from the subject is selected from the group consisting of blood, a blood product, urine, saliva, cerebrospinal fluid, stool, tissue sample and lymph.

In a twelfth embodiment of the second aspect which is also an embodiment of the eleventh embodiment of the second aspect, the sample from the subject is selected from the group consisting of blood and a blood product.

In a thirteenth embodiment of the second aspect which is also an embodiment of the eleventh and the twelfth embodiment of the second aspect, the blood product is selected from the group comprising serum and plasma.

In a fourteenth embodiment of the second aspect which is also an embodiment of the first, the second, the third, the fourth, the fifth, the sixth, the seventh, the eighth, the ninth, the tenth, the eleventh, the twelfth and the thirteenth embodiment of the second aspect and of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third and the twenty-fourth embodiment of the first aspect, preferably of the thirteenth embodiment of the second aspect, the method has a limit of detection of 0.2 ng/ml.

In a fifteenth embodiment of the second aspect which is also an embodiment of the first, the second, the third, the fourth, the fifth, the sixth, the seventh, the eighth, the ninth, the tenth, the eleventh, the twelfth, the thirteenth and the fourteenth embodiment of the second aspect and of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third and the twenty-fourth embodiment of the first aspect, preferably of any of the eleventh, the twelfth, the thirteenth, the fourteenth and the fifteenth embodiment of the second aspect, the cut-off level is 5.0 ng/ml.

In a sixteenth embodiment of the second aspect which is also an embodiment of the eleventh and the twelfth embodiment of the second aspect, the blood is whole blood.

In an seventeenth embodiment of the second aspect which is also an embodiment of the seventeenth embodiment of the second aspect, the whole blood is collected on a dry blood filter card.

In an eighteenth embodiment of the second aspect which is also an embodiment of the seventeenth and the eighteenth embodiment of the second aspect, the method has a limit of detection of 0.2 ng/ml.

In a nineteenth embodiment of the second aspect which is also an embodiment of the seventeenth, the eighteenth and the nineteenth embodiment of the second aspect, the cut-off level is 20.0 ng/ml.

The problem underlying the present invention is solved in a third aspect which is also the first embodiment of the third aspect, by a method for determining the course of Gaucher's disease in a subject comprising the step of
  a) determining at several points in time a level of a biomarker present in a sample from the subject, wherein the biomarker is free lyso-Gb1.

In a second embodiment of the third aspect which is also an embodiment of the first embodiment of the third aspect, the subject has been previously treated or diagnosed for Gaucher's disease.

In a third embodiment of the third aspect which is also an embodiment of the first embodiment of the third aspect, the subject has not been previously treated or wherein the subject has not been previously diagnosed for Gaucher's disease.

In a fourth embodiment of the third aspect which is also an embodiment of the first, the second and the third embodiment of the third aspect, the method further comprises a step of
  b) applying, maintaining, reducing, elevating or not applying a therapy based on the diagnosis of whether the subject is suffering from or for being at risk for developing Gaucher's disease.

In a fifth embodiment of the third aspect which is also an embodiment of the first, the second, the third and the fourth embodiment of the third aspect, the method further comprises a step of
  c) detecting the biomarker in a sample from the subject after applying, maintaining, reducing, elevating or not applying a therapy in a step of b).

In a sixth embodiment of the third aspect which is also an embodiment of the first, the second, the third, the fourth and the fifth embodiment of the third aspect, the method further comprises a step of
  d) determining a level of the biomarker in the sample from the subject after applying, maintaining, reducing, elevating or not applying a therapy in a step of b).

In a seventh embodiment of the third aspect which is also an embodiment of the first, the second, the third, the fourth, the fifth and the sixth embodiment of the third aspect, the method further comprises the steps of
  e) determining whether the level of the biomarker determined in step a) is lower than the level of the biomarker determined in step d);

In an eighth embodiment of the third aspect which is also an embodiment of the seventh embodiment of the third aspect, the method further comprises the step of
  f) applying, maintaining, reducing, elevating or not applying a therapy based on the step of e).

In a ninth embodiment of the third aspect which is also an embodiment of the first, the second, the third, the fourth, the fifth, the sixth, the seventh and the eighth embodiment of the third aspect, the method further comprises detecting at least one additional biomarker in the sample from the subject.

In a tenth embodiment of the third aspect which is also an embodiment of the ninth embodiment of the third aspect, the method further comprises determining the level of the at least one additional biomarker in the sample from the subject.

In an eleventh embodiment of the third aspect which is also an embodiment of the ninth and the tenth embodiment of the third aspect, the at least one additional biomarker is selected from the group comprising chitotriosidase and CCL18.

In a twelfth embodiment of the third aspect which is also an embodiment of the eleventh embodiment of the third aspect, the at least one additional biomarker is chitotriosidase.

In a thirteenth embodiment of the third aspect which is also an embodiment of the eleventh embodiment of the third aspect, the at least one additional biomarker is CCL18.

In a fourteenth embodiment of the third aspect which is also an embodiment of the first, the second, the third, the fourth, the fifth, the sixth, the seventh, the eighth, the ninth, the tenth, the eleventh, the twelfth and the thirteenth embodiment of the third aspect, the method further comprises detecting chitotriosidase and CCL18.

In a fifteenth embodiment of the third aspect which is also an embodiment of the first, the second, the third, the fourth, the fifth, the sixth, the seventh, the eighth, the ninth, the tenth, the eleventh, the twelfth, the thirteenth and the fourteenth embodiment of the third aspect, the biomarker and/or the at least one additional biomarker is detected by means of immunoassay, mass spectrometric analysis, biochip array, functional nucleic acids and/or a fluorescent derivative of free lyso-Gb1.

In a sixteenth embodiment of the third aspect which is also an embodiment of the fifteenth embodiment of the third aspect, the biomarker is detected by means of mass spectrometric analysis.

In a seventeenth embodiment of the third aspect which is also an embodiment of the sixteenth embodiment of the third aspect, mass spectrometric analysis is selected from the group consisting of SELDI, MALDI, MALDI-Q TOF, MS/MS, TOF-TOF and ESI-O-TOF.

In an eighteenth embodiment of the third aspect which is also an embodiment of the seventeenth embodiment of the third aspect, the mass spectrometric analysis uses MS/MS.

In a nineteenth embodiment of the third aspect which is also an embodiment of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth and the eighteenth embodiment of the third aspect, the method further comprises protein precipitation and/or HPLC.

In a twentieth embodiment of the third aspect which is also an embodiment of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth and the nineteenth embodiment of the third aspect, the method further comprises protein precipitation, HPLC and MS/MS.

In a twenty first embodiment of the third aspect which is also an embodiment of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth and the twenty first embodiment of the third aspect, the subject is a human.

In a twenty second embodiment of the third aspect which is also an embodiment of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty first and the twenty second embodiment of the third aspect, the step of detecting the biomarker in the sample from the subject comprises precipitating protein from the sample from the subject, wherein precipitating protein from the sample provides a supernatant of the sample; subjecting a volume of the supernatant to HPLC and MS/MS and determining the amount of the biomarker and/or the at least one additional biomarker that is/are present in the sample from the subject.

In a twenty third embodiment of the third aspect which is also an embodiment of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty first, the twenty second and the twenty third embodiment of the third aspect, Gaucher's disease is selected from the group comprising the non-neuronopathic type I, the chronic neuronopathic type II and the acute neuronopathic type III.

The problem underlying the present invention is solved in a fourth aspect which is also the first embodiment of the fourth aspect, by a method for determining the effectiveness of at least one treatment applied to a subject being positively tested for suffering from or being at risk for developing Gaucher's disease comprising the step of
  a) determining at several points in time a level of a biomarker present in a sample from the subject,
wherein the biomarker is free lyso-Gb1.

In a second embodiment of the fourth aspect which is also an embodiment of the first embodiment of the fourth aspect, the subject has been previously treated or diagnosed for Gaucher's disease.

In a third embodiment of the fourth aspect which is also an embodiment of the first embodiment of the fourth aspect, the subject has not been previously treated or wherein the subject has not been previously diagnosed for Gaucher's disease.

In a fourth embodiment of the fourth aspect which is also an embodiment of the first, the second and the third embodiment of the fourth aspect, the method further comprises a step of
  b) applying, maintaining, reducing, elevating or not applying at least one treatment applied to the subject based on the decrease in the level of the biomarker.

In a fifth embodiment of the fourth aspect which is also an embodiment of the first, the second, the third and the fourth embodiment of the fourth aspect, the method further comprises a step of
  c) detecting the biomarker in the sample from the subject, wherein the sample has been taken prior to the beginning of the treatment after applying, maintaining, reducing, elevating or not applying at least one treatment in a step of b).

In a sixth embodiment of the fourth aspect which is also an embodiment of the first, the second, the third, the fourth and the fifth embodiment of the fourth aspect, the treatment is selected from the group comprising enzyme replacement therapy, substrate reduction therapy, chaperone therapy, gene therapy, stem cell transplantation of DNA/RNA skipping.

In a seventh embodiment of the fourth aspect which is also an embodiment of the first, the second, the third, the fourth, the fifth and the sixth embodiment of the fourth aspect, the method further comprises the steps of
  d) determining whether the level of the biomarker determined in step a) is lower than the level of the biomarker determined in step c).

In an eighth embodiment of the fourth aspect which is also an embodiment of the seventh embodiment of the fourth aspect, the method further comprises the steps of
  e) applying, maintaining, reducing, elevating or not applying at least one treatment applied to the subject based on the step of d).

In a ninth embodiment of the fourth aspect which is also an embodiment of the first, the second, the third, the fourth, the fifth, the sixth, the seventh and the eighth embodiment of the fourth aspect, the method further comprises detecting at least one additional biomarker in the sample from the subject.

In a tenth embodiment of the fourth aspect which is also an embodiment of the ninth embodiment of the fourth aspect, the method further comprises determining the level of the at least one additional biomarker in the sample from the subject.

In an eleventh embodiment of the fourth aspect which is also an embodiment of the ninth and the tenth embodiment of the fourth aspect, the at least one additional biomarker is selected from the group comprising chitotriosidase and CCL18.

In a twelfth embodiment of the fourth aspect which is also an embodiment of the eleventh embodiment of the fourth aspect, the at least one additional biomarker is chitotriosidase.

In a thirteenth embodiment of the fourth aspect which is also an embodiment of the eleventh h embodiment of the fourth aspect, the at least one additional biomarker is CCL18.

In a fourteenth embodiment of the fourth aspect which is also an embodiment of the first, the second, the third, the fourth, the fifth, the sixth, the seventh, the eighth, the ninth, the tenth, the eleventh, the twelfth and the thirteenth embodiment of the fourth aspect, the method further comprises detecting chitotriosidase and CCL18.

In a fifteenth embodiment of the fourth aspect which is also an embodiment of the first, the second, the third, the fourth, the fifth, the sixth, the seventh, the eighth, the ninth, the tenth, the eleventh, the twelfth, the thirteenth and the fourteenth embodiment of the fourth aspect, any/the biomarker is detected by means of immunoassay, mass spectrometric analysis, biochip array, functional nucleic acids and/or a fluorescent derivative of free lyso-Gb1.

In a sixteenth embodiment of the fourth aspect which is also an embodiment of the fifteenth embodiment of the fourth aspect, the biomarker is detected by means of mass spectrometric analysis.

In a seventeenth embodiment of the fourth aspect which is also an embodiment of the sixteenth embodiment of the fourth aspect, mass spectrometric analysis is selected from the group consisting of SELDI, MALDI, MALDI-Q TOF, MS/MS, TOF-TOF and ESI-O-TOF.

In an eighteenth embodiment of the fourth aspect which is also an embodiment of the seventeenth embodiment of the fourth aspect, the mass spectrometric analysis uses MS/MS.

In a nineteenth embodiment of the fourth aspect which is also an embodiment of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth and the eighteenth embodiment of the fourth aspect, the method further comprises protein precipitation and/or HPLC.

In a twentieth embodiment of the fourth aspect which is also an embodiment of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth and the nineteenth embodiment of the fourth aspect, the method further comprises protein precipitation, HPLC and MS/MS.

In a twenty-first embodiment of the fourth aspect which is also an embodiment of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth and the twentieth embodiment of the fourth aspect, the subject is a human.

In a twenty-second embodiment of the fourth aspect which is also an embodiment of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth and the twenty-first embodiment of the fourth aspect, the step of detecting the biomarker in the sample from the subject comprises precipitating protein from the sample from the subject, wherein precipitating protein from the sample provides a supernatant of the sample; subjecting a volume of the supernatant to HPLC and MS/MS and determining the amount of the biomarker and/or the at least one additional biomarker that is/are present in the sample from the subject.

In a twenty-third embodiment of the fourth aspect which is also an embodiment of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first and the twenty-second embodiment of the fourth aspect, Gaucher's disease is selected from the group comprising the non-neuronopathic type I, the chronic neuronopathic type II and the acute neuronopathic type III.

The problem underlying the present invention is solved in a fifth aspect which is also the first embodiment of the fifth aspect, by a method of determining the effectiveness of a compound for the treatment of Gaucher's disease comprising the steps of:
   a) determining a level of a biomarker in a subject having Gaucher's disease;
   b) administering to said subject said compound;
   c) determining again the level of the biomarker in said subject;
   d) determining whether the level of the biomarker determined in step a) is lower than the level of the biomarker determined in step c),
wherein a level of the biomarker determined in step c) which is lower than the level of the biomarker determined in step a) indicates the effectiveness of said compound, and wherein the biomarker is free lyso-Gb1.

In a second embodiment of the fifth aspect which is also an embodiment of the first embodiment of the fifth aspect, the method further comprises determining a level of the biomarker in a control.

In a third embodiment of the fifth aspect which is also an embodiment of the first and the second embodiment of the fifth aspect, Gaucher's disease is selected from the group comprising the non-neuronopathic type I, the chronic neuronopathic type II and the acute neuronopathic type III.

The problem underlying the present invention is solved in a sixth aspect which is also the first embodiment of the sixth aspect, by the use of mass spectrometry for the detection of a biomarker, wherein the biomarker is free lyso-Gb1.

In a second embodiment of the sixth aspect which is also an embodiment of the first embodiment of the sixth aspect, the detection comprises the use of HPLC.

In a third embodiment of the sixth aspect which is also an embodiment of the first and the second embodiment of the sixth aspect, the detection comprises MS/MS.

The problem underlying the present invention is solved in a seventh aspect which is also the first embodiment of the seventh aspect, by the use of a biomarker for Gaucher's disease, preferably in a method according to any one of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third and the twenty-fourth embodiment of the first aspect, of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth and the nineteenth embodiment of the second aspect, of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second and the twenty-third embodiment of the third aspect, of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second and the twenty-third embodiment of the fourth aspect and of the first, the second and the third embodiment of the fifth aspect, wherein the biomarker is free lyso-Gb1.

In a second embodiment of the seventh aspect which is also an embodiment of the first embodiment of the seventh aspect, Gaucher's disease is selected from the group comprising the non-neuronopathic type I, the chronic neuronopathic type II and the acute neuronopathic type III.

The problem underlying the present invention is solved in a eighth aspect which is also the first embodiment of the eight aspect, by a kit for determining the presence of a biomarker in a sample from a subject, wherein the kit comprises
   a) an interaction partner of the biomarker;
   b) optionally a solid support comprising at least one capture reagent attached thereto, wherein the capture reagent binds the biomarker; and
   c) instructions for using the solid support to detect the biomarker,
wherein the biomarker is free lyso-Gb1.

In a second embodiment of the eighth aspect which is also an embodiment of the first embodiment of the eighth aspect, the kit is for
   a) diagnosing Gaucher's disease;
   b) determining the course of Gaucher's disease in a subject; and/or
   c) determining the effectiveness of at least one treatment applied to a subject,
wherein a method applied in a), b) and/or c) is preferably a method according to any one of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second, the twenty-third and the twenty-fourth embodiment of the first aspect, of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth and the nineteenth embodiment of the second aspect, of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second and the twenty-third embodiment of the third aspect, of the first, the second, the third, the fourth, the fifth, the sixth, the seventh, the eighth, the ninth, the tenth, the eleventh, the twelfth, the thirteenth, the fourteenth, the fifteenth, the sixteenth, the seventeenth, the eighteenth, the nineteenth, the twentieth, the twenty-first, the twenty-second and the twenty-third embodiment of the fourth aspect and of the first, the second and the third embodiment of the fifth aspect.

In a third embodiment of the eighth aspect which is also an embodiment of the first and the second embodiment of the eighth aspect, Gaucher's disease is selected from the group comprising the non-neuronopathic type I, the chronic neuronopathic type II and the acute neuronopathic type III.

The problem underlying the present invention is solved in a ninth aspect which is also the first embodiment of the ninth aspect, by a software product comprising
  a) code that accesses data attributed to a sample, the data comprising detection of at least one biomarker in the sample, the biomarker selected from the group comprising free lyso-Gb1, Chitotriosidase and CCL18; and
  b) code that executes a classification algorithm that classifies Gaucher's disease status of the sample as a function of the detection.

In a second embodiment of the ninth aspect which is also an embodiment of the first embodiment of the ninth aspect, Gaucher's disease is selected from the group comprising the non-neuronopathic type I, the chronic neuronopathic type II and the acute neuronopathic type III.

The present inventors have surprisingly found that free lyso-Gb1 constitutes a biomarker which allows for a method for diagnosing Gaucher's disease in a subject, more specifically diagnosing Gaucher's disease in a subject with high specificity and sensitivity using said free lyso-Gb1 as the biomarker.

The present inventors have also surprisingly found that free lyso-Gb1, which can be detected by the methods of the present invention, is circulating in the blood of a subject in a concentration of approximately 1/1000 of total Gb1. Moreover, the present inventors have surprisingly found that, unlike total Gb1, free lyso-Gb1 which is present in the blood of a subject is useful in a method for diagnosing Gaucher's disease in a subject comprising a step of detecting a biomarker in a sample from the subject, wherein the biomarker is free lyso-Gb1. The present inventors have also surprisingly found that the level of free lyso-Gb1 determined in the sample from a subject by the methods of the present invention allows for diagnosing Gaucher's disease with high sensitivity and high specificity.

In so far the present invention turns away from the teaching of the state of the art in that the method of the present invention comprises determining the level of a lyso-compound using said lyso-compound as a biomarker for diagnosis of a sphingolipidoses. More specifically, the present inventors have surprisingly found that determining the level of free lyso-Gb1 in a sample from a subject allows for diagnosing Gaucher's disease with high sensitivity and high specificity.

It is also the merit of the present inventors of having recognized that a fraction of total Gb1 which is accumulated in Gaucher's disease, is present as a molecule in a free lyso form thereof, i.e. free lyso-Gb1, and is circulating in the blood of a subject in said free lyso form besides Gb1.

The term "lysosomal storage disorder", also referred to as "lysosomal storage disease" or "LSD", as used herein, preferably refers to genetic diseases and metabolic disorders that result from defects in lysosomal function. Lysosomal storage disorders are caused by lysosomal dysfunction usually as a consequence of deficiency of a single enzyme required for the metabolism of lipids, glycoproteins or so-called mucopolysaccharides. Like other genetic diseases, individuals inherit lysosomal storage diseases from their parents. Although each disorder results from different gene mutations that translate into a deficiency in enzyme activity, they all share a common biochemical characteristic—all lysosomal disorders originate from an abnormal accumulation of substances inside the lysosome.

The term "Gaucher's disease" as used herein, preferably refers to a lysosomal storage disease (LSD), more specifically a sphingolipidoses that is characterized by the deposition of glucocerebroside in cells of the macrophage-monocyte system. Gaucher's disease is the most common of the lysosomal storage diseases (James, William D.; Berger, Timothy G.; et al. (2006). *Andrews' Diseases of the Skin: clinical Dermatology*. Saunders Elsevier. ISBN 0-7216-2921-0). It is caused by a hereditary deficiency of the enzyme glucocerebrosidase. Said deficiency results from recessive mutation(s) in the gene coding for glucocerebrosidase, a specific lysosomal hydrolase (also known as beta-glucosidase, EC 3.2.1.45, PDB 1OGS) located on chromosome 1 (1q21) and affects both males and females. Different mutations in the beta-glucosidase determine the remaining activity of the enzyme, and, to a large extent, the phenotype.

Glucocerebrosidase is also referred to herein as β-glucocerebrosidase, beta-glucosidase, acid beta-glucosidase, glucosylceramidase or D-glucosyl-N-acylsphingosine glucohydrolase. The enzyme is a 55.6 KD, 497 amino acids long protein having glucosylceramidase activity, i.e. the enzyme catalyses the breakdown of a fatty substance called glucocerebroside by cleavage, i.e. hydrolysis, of a beta-glucosidic linkage of glucocerebroside, which is an intermediate in glycolipid metabolism. Glucocerebroside, also referred to herein as glucosylceramide or Gb1, is a cell membrane constituent of red and white blood cells. When the enzyme is defective, the substance accumulates, particularly in cells of the mononuclear cell lineage. This is because macrophages that clear these cells are unable to eliminate the waste product, which accumulates in fibrils, and turn into so called Gaucher cells, which appear on light microscopy to resemble crumpled-up paper. Fatty material can accumulate in the spleen, liver, kidneys, lungs, brain and bone marrow.

Gaucher's disease has three common clinical subtypes.

Non-neuronopathic type I, also referred to herein as type I, is the most common form of the disease, occurring in approximately 1 in 50,000 live births. It occurs most often among persons of Ashkenazi Jewish heritage. Symptoms may begin early in life or in adulthood and include enlarged liver and grossly enlarged spleen (together hepatosplenomegaly); the spleen can rupture and cause additional complications. Skeletal weakness and bone disease may be extensive. Spleen enlargement and bone marrow replacement cause anemia, thrombocytopenia and leukopenia. The brain is not affected pathologically, but there may be lung and, rarely, kidney impairment. Diseased subjects in this group usually bruise easily (due to low levels of platelets) and experience fatigue due to low numbers of red blood cells. Depending on disease onset and severity, type I patients may live well into adulthood. Many diseased subjects have a mild form of the disease or may not show any symptoms.

Chronic neuronopathic type II, also referred to herein as type II, can begin at any time in childhood or even in adulthood, and occurs in approximately 1 in 100,000 live births. It is characterized by slowly progressive but milder neurologic symptoms compared to the acute or type III version. Major symptoms include an enlarged spleen and/or liver, seizures, poor coordination, skeletal irregularities, eye movement disorders, blood disorders including anemia and respiratory problems. Patients often live into their early teen years and adulthood.

Acute neuronopathic type III, also referred to herein as type III, typically begins within 6 months of birth and has an incidence rate of approximately 1 in 100,000 live births. Symptoms include an enlarged liver and spleen, extensive and progressive brain damage, eye movement disorders, spasticity, seizures, limb rigidity, and a poor ability to suck and swallow. Affected children usually die by age 2.

These subtypes have come under some criticism for not taking account of the full spectrum of observable symptoms. There are also compound heterozygous variations which considerably increase the complexity of predicting disease course.

In type II and III of Gaucher's disease, glucocerebroside accumulates the brain due to the turnover of complex lipids during brain development and the formation of the myelin sheath of nerves.

Symptoms may include enlarged spleen and liver, liver malfunction, skeletal disorders and bone lesions that may be painful, severe neurologic complications, swelling of lymph nodes and (occasionally) adjacent joints, distended abdomen, a brownish tint to the skin, anemia, low blood platelets and yellow fatty deposits on the white of the eye (sclera). Persons affected most seriously may also be more susceptible to infection.

Therapy: Enzyme replacement treatment also referred to herein as ERT, is the therapy of choice. However, successful bone marrow transplantation might cure the non-neurological manifestations of the disease, because it introduces a monocyte population with active beta-glucosidase. It is important to mention that this procedure carries significant risk and is rarely performed in Gaucher's disease patients. Surgery to remove the spleen (splenectomy) may be very rarely required if the patient is massively anemic or when the enlarged organ affects the patient's comfort. Blood transfusion may benefit some anemic patients. Other patients may require joint replacement surgery to improve mobility and quality of life. Other treatment options include antibiotics for infections, antiepileptics for seizures, bisphosphonates for bone lesions, and liver transplants.

ERT is based on chronic intravenous administration of a recombinant glucocerebrosidase (imiglucerase, Genzyme; velaglucerase, Shire; taliglucerase, Protalix) (G. A. Grabowski et al., Enzyme therapy in type I Gaucher's disease: comparative efficacy of mannose-terminated glucocerebrosidase from natural and recombinant sources, Ann. Intern. Med. 122 (1995) 33-39.). For type I and most type III patients, ERT with intravenous recombinant glucocerebrosidase (such as, e.g., imiglucerase) can significantly reduce liver and spleen size, reduce skeletal abnormalities, and reverse other manifestations.

More recently substrate reduction therapy also referred to herein as SRT, has been developed as an alternative treatment for Gaucher's disease (F. M. Platt et al. N-butyl-deoxynojirimycin is a novel inhibitor of glycosphingolipid biosynthesis, J. Biol. Chem. 269 (1994) 8362-8365.). Partial inhibition of glycosphingolipid synthesis with N-butyl-deoxynojirimycin (miglustat, Actelion) is employed in an effort to balance the reduced catabolic capacity in Gaucher's disease patients. SRT may prove to be effective in stopping type II, as it can cross through the blood barrier into the brain. There is currently no effective treatment for the severe brain damage that may occur in patients with types II and III Gaucher's disease.

Both ERT and SRT generally result in marked clinical improvements such as reduction in hepatosplenomegaly, corrections in hematological abnormalities, stabilization or improvement in skeletal deterioration.

Glucocerebroside, also referred to herein as glucosylceramide or Gb1, means any cerebroside in which the monosaccharide head group is glucose.

It will be understood by a person skilled in the art that the term "lyso-Gb1" as used herein, preferably in connection with the various methods, preferably means that the molecule is present in its free amino form. More precisely, lyso-Gb1 as used herein, preferably differs from Gb1 in that no fatty acid moiety is linked to the primary amino group of the sphingosine moiety of the molecule. Furthermore, lyso-Gb1 is also referred to herein as glucosylsphingosine or lyso-glucocerebroside and has the formula:

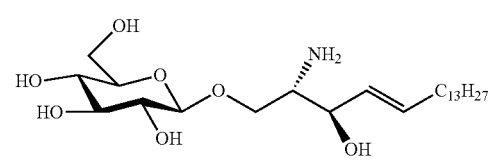

(I)

It will be understood by a person skilled in the art that the term "free lyso-Gb1" as used herein preferably refers to lyso-Gb1 which is as such present in a sample from the subject, such as blood, and, preferably, not the result of a manipulation of the sample of said subject. Such manipulation of a sample can be the one described by Groener et al. (Groener et al. Plasma glucosylceramide and ceramide in type 1 Gaucher disease patients: Correlations with disease severity and response to therapeutic intervention. Biochimica et Biophysica Acta 1781(2908)72 78, 2007). In accordance therewith, free lyso-Gb1 which is present as such in the blood of a subject from whom the sample is taken, is more particularly not a lyso-Gb1 which is generated by chemical, biochemical or physical treatment of the sample contained in the blood and sample, respectively, preferably outside of the body of the patient. It will be also understood by a person skilled in the art that free lyso-Gb1 as used herein, preferably is present in addition to Gb1 and is a compound produced by the subject's metabolic activities. Accordingly, Gb1, which is the molecule that is accumulated in connection with Gaucher's disease is present in the sample from the subject has compared to the molecule in a free lyso form, i.e. free-lyso-Gb1, present in the blood of the subject at least one fatty acid moiety linked to the primary amino group of the sphingosine moiety of lyso-Gb1.

The term "sample" as preferably used herein means a limited quantity of a subject's material, wherein said subject's material is part of or has been taken from a subject and/or a subject's body and wherein said material is selected from the group comprising body fluids such as blood, a blood product, urine, saliva, cerebrospinal fluid and lymph, as well as stool or any kind of tissue and or cell material being part of a subject and/or a subject's body. It will be acknowledged by a person skilled in the art, that the presence of and/or a level of a biomarker of the invention in said sample is intended to be similar to and represent the presence and/or the level of the biomarker in a larger amount of that subject's material. More precisely and as an illustrative, non-limiting example, a level of a biomarker of the invention determined in a sample of some ml of blood from a subject also represents a level of said biomarker in the blood of the subject's body. Furthermore, in an embodiment of the method of the invention for diagnosing Gaucher's disease in a subject, a sample from the subject comprises said subject's material in a form, for example processed, fixed and/or preserved such that said sample is suitable for use in the method of the invention, whereby such processing, fixing and/or preserving preferably does not generate lyso-Gb1. The subject's material in the sample may thus be diluted, for example with a solvent suitable for the method of the invention such as methanol and/or water, may be dried, for example on a filter card, may be resolved after having been dried such, for example with a solvent suitable for the method of the invention such as methanol and/or water, or a substance may be added, wherein said substance prevents blood from coagulation such as for example EDTA or heparin. It will be further understood by a person skilled in the art that the method of the invention comprises that said subject's material is separated into single components of said subject's material and/or single components of said subject's material are extracted from said subject's material, for example blood is separated into plasma or serum and cellular blood components or protein is precipitated from the sample. It will be immediately understood that after such processing, fixing and/or preserving the sample is subjected to the methods of the invention for detecting and/or determining the level of a biomarker contained in said sample whereby such processing, fixing and/or preserving preferably does not generate lyso-Gb1.

In an embodiment of the method of the present invention wherein whole blood is collected on a dry blood filter card preferably approximately 3 µl of full blood are collected on a spot of said dry blood filter card having a diameter of 3 mm A person skilled in the art will acknowledge that the exact volume thus collected may vary depending on the hematocrit of the specific patient.

The levels of glucosylceramide and its precursor ceramide were used in the prior art to correlate their presence in plasma with the severity of Gaucher's disease type I and the response to the application of therapy (Groener et al., Plasma glucosylceramide and ceramide in type 1 Gaucher's disease patients: Correlations with disease severity and response to therapeutic intervention. Biochimica et Biophysica Acta 1781(2908)72~78, 2007). Thereby, the level of Gb1 was found to be different although ceramide levels were not significantly different in the plasma of treated and untreated Gaucher's disease type I patients.

In the study reported by Groener et al. (Groener et al., supra) the ratio of Gb1/ceramide was used to discriminate between Gaucher's disease patients and healthy patients. Gb1 and ceramide were measured with high performance liquid chromatography (HPLC) essentially as described in Groener et al. (J. E. M. Groener et al., HPLC for simultaneous quantification of total ceramide, glucosylceramide, and ceramide trihexoside concentrations in plasma, Clin. Chem. 53 (2007) 742-747). In connection therewith it is important to understand that Gb1 present in the plasma mainly consists of a sugar moiety and a ceramide moiety. The ceramide moiety comprising a sphingosine and a fatty acid moiety. According to the method of the prior art lipids are extracted and ceramide and glucosylceramide are deacylated by alkaline hydrolysis thus forming the lyso form, i.e. lyso-Gb1 (T. Taketomi et al., Rapid method of preparation of lysoglycosphingolipids and their confirmation by delayed extraction matrix-assisted laser desporption ionization time-of-flight mass spectrometry, J. Biochem. (Tokyo) 120 (1996) 573-579). Subsequently, the thus produced lyso-Gb1 is labeled with a fluorescence dye by derivatization with O-phthaldialdehyde (OPA) at the primary amine group. Afterwards the derivatized sphingoid bases were separated by reverse phase HPLC and detected with a fluorescence detector. Thus said method of the prior art is able to detect total Gb1 consisting of free lyso-Gb1 and Gb1 and is not able to distinguish a level of free lyso-Gb1 from a level of Gb1 in a sample from a subject. The level of said total Gb1 after cleavage of the various fatty acid moieties from the NH2 group of the Gb1 is usually in a range of from 5 to 30 µg per mL plasma or serum. From this it is evident that in the method of Groener et al. (Groener et al., supra) the total-Gb1 which can be prepared and obtained, respectively, from a sample, preferably a blood sample, from a subject is used as a biomarker rather than the free lyso-Gb1 contained in the blood and accordingly also in the sample without performing a cleavage of the fatty acid moiety/moieties, preferably a cleavage performed by an operator handling the sample. Insofar, the present invention is related to the detection of free lyso-Gb1 rather than total-Gb1 as taught in the prior art. It is an embodiment of the methods of the present invention comprising detecting and/or determining the level of free lyso-Gb1 in a sample from a subject that free lyso-Gb1 and/or the level of free lyso-Gb1 is determined separate from and/or apart from Gb1 or a level of Gb1 which may be present in the blood of a subject. In a further embodiment Gb1 and/or a level of Gb1 is detected/determined in addition to the detection of and/or the determining of a level of free lyso-Gb1.

Importantly, each primary amine circulating in the plasma and being sufficiently lipophilic to be extracted concomitantly with Gb1 using an organic solvent according to said method of the art is labeled accordingly and thus is able to disturb the detection of cleaved lyso-Gb1.

Although total Gb1 measured as lyso-Gb1 in said study of the prior art was increased in plasma of said patients, said increase in total Gb1 was not prominent and thus the specificity and the sensitivity of the method were low showing that Gb1 is not suitable as a biomarker for Gaucher's disease.

In connection therewith it is important to note that to the knowledge of the inventors the data described in the Examples herein in connection with the present invention represent the first systematic analysis of specificity and sensitivity with regard to a direct comparison of biomarkers for Gaucher's disease of the prior art, i.e. chitotriosidase and CCL18, and of free lyso-Gb1.

Providing a sensitivity and/or specificity of ≥99.0% free lyso-Gb1 as determined by the methods of the present invention is a biomarker suitable of clinical application in connection with Gaucher's disease. Insofar, the biomarker of the present invention and uses thereof clearly exceed the performance of biomarkers known the prior art, more specifically, the one of chitotriosidase and CCL18. It will be immediately understood that also the method applied by Groener et al. (Groener et al., supra) is prejudicial compared to the methods of the present invention in that the specificity and sensitivity of said method of the prior art is lower and diagnosing of Gaucher's disease based on such method of the prior art using total Gb1 rather than free lyso-Gb1 is not suitable for reliable clinical application thereof, i.e. the method has no sensitivity and specificity sufficient to diagnose Gaucher's disease by a reliable statistically secured prediction.

Chitotriosidase: It has been found previously that Gaucher cells secrete chitotriosidase and that chitotriosidase in plasma of symptomatic patients with Gaucher's disease is elevated on average several hundred-fold (Hollak et al. Marked elevation of plasma chitotriosidase activity. A novel hallmark of Gaucher disease. J Clin Invest. 1994; 93: 1288-1292). Therefore, plasma chitotriosidase is used therefore as a surrogate marker for Gaucher's disease manifestations and is used for diagnosis, early determination of onset of disease, and monitoring of therapeutic efficacy (Hollak et al. Marked elevation of plasma chitotriosidase activity. A novel hallmark of Gaucher disease. J Clin Invest. 1994; 93: 1288-1292; Mistry et al. A practical approach to diagnosis and management of Gaucher's disease. Baillieres Clin Haematol. 1997; 10: 817-838; Cox et al. Novel oral treatment of Gaucher's disease with N-butyldeoxynojirimycin (OGT 918) to decrease substrate biosynthesis. Lancet. 2000; 355: 1481-1485; Hollak et al. Clinically relevant therapeutic endpoints in type I Gaucher disease. J Inherit Metab Dis. 2001; 24: 97-105).

Nevertheless, plasma chitotriosidase levels do not reflect one particular clinical symptom, but rather are a reflection of the total body burden of Gaucher cells (Aerts et al. Plasma and metabolic abnormalities in Gaucher's disease. Baillieres Clin Haematol. 1997; 10: 691-709); furthermore it is not reflecting the burden of the disease driven by the bone pathology and the brain damage. The level of chitotriosidase is not directly linked to the pathophysiology of Gaucher's disease. Additionally, after treatment the level of chitotriosidase changes extremely slowly making chitotriosidase unsuitable for assessing quickly the efficacy of treatment to which the patient is or has been subjected as well as a relapse of the disease independent form the cause of the disease.

Furthermore, the use of plasma chitotriosidase as a Gaucher cell marker is hampered by the fact that patients, including those with Gaucher's disease, may be deficient in chitotriosidase activity due to a 24-base pair (bp) duplication in the chitotriosidase gene. Obviously these individuals cannot be monitored by the measurement of plasma chitotriosidase activity (Hollak et al. Marked elevation of plasma chitotriosidase activity. A novel hallmark of Gaucher disease. J Clin Invest. 1994; 93: 1288-1292; Boot et al. The human chitotriosidase gene. Nature of inherited enzyme deficiency. J Biol Chem. 1998; 273: 25680-25685). The frequency of the 24-bp duplication in the chitotriosidase gene depends on the ethnicity and can raise up to nearly 35% (Prof. Guiliani, Brasil, unpublished data).

CCL18: The glucosylceramide-laden macrophages or Gaucher cells are the main source of CCL18. The level of CCL18 in the plasma of patients having Gaucher's disease is significantly increased (Boot, R. G. et al. 2004. Marked elevation of the chemokine CCL18/PARC in Gaucher disease: a novel surrogate marker for assessing therapeutic intervention. Blood 103:33-39.). Therefore there were attempts to use the level of CCL18 in the plasma as a surrogate marker for monitoring the success of a therapy applied. Nevertheless, elevated levels of CCL18 were also found to be associated with a variety of disease, such as different types of cancer and inflammation of joints, lungs and skin. For example, ascites of patients having ovarian carcinoma contains a significantly elevated level of CCL18 compared to patients without ovarian carcinoma (Budd-Chiari syndrome) (Schutyser, E. et al. 2002. Identification of biologically active chemokine isoforms from ascitic fluid and elevated levels of CCL18/pulmonary and activation-regulated chemokine in ovarian carcinoma. J Biol. Chem. 277:24584-24593.). CCL18 plays a role in tumor suppression since it attracts and activates specific immune cells. Furthermore children having acute lymphocytic leukemia are found to exhibit elevated levels of CCL18, whereas children having acute myeloid leukemia do not show elevated serum levels of CCL18 (Struyf, S et al. 2003. ARC/CCL18 is a plasma CC chemokine with increased levels in childhood acute lymphoblastic leukemia. Am J Pathol. 163: 2065-2075.). Again plasma CCL18 levels do not reflect one particular clinical symptom, but rather are a reflection of the total body burden of Gaucher cells. As can be seen from the above CCL18 exhibits an extremely low specificity for the diagnosis of Gaucher's disease and is thus mainly applied as a "auxiliary" surrogate marker for patients deficient in chitotriosidase activity.

In connection with the use of chitotriosidase and CCL18 it is to be noted that chitotriosidase fails testing positive in 10-30% of all patients, i.e. patients are tested negative although suffering from Gaucher's disease and thus also the application of a therapy will be renounced. Furthermore, in these cases the marker cannot further be used as a follow-up marker for monitoring, e.g., ERT. If it is suspected that the patient is affected by the defect of chitotriosidase, CCL18 is used as a biomarker for diagnosing Gaucher's disease, whereby a method making use of CCL18 as a biomarker exhibits relatively low specificity and sensitivity, i.e. diagnoses false positive or false negative in about 25% of all patients.

The term "Gaucher's disease status" as used herein, preferably refers to the status of the disease in the subject. Examples of types of Gaucher's disease statuses include, but are not limited to, the subject's risk of suffering or developing Gaucher's disease, the stage of the disease in a subject and the effectiveness of treatment of the disease. Other statuses and degrees of each status are known in the art. In an embodiment of the present invention the Gaucher's disease status comprises a severe, mild, or healthy Gaucher's disease status.

The term "diagnosing" as used herein, preferably means determining the presence or the absence of a disease or disorder in a subject and/or determining whether a subject is at risk for developing a disease, a disorder or symptoms related to a disease or disorder as well as predicting a status of a disease.

The term "detecting" in the context of the present invention means methods which include detecting the presence or absence of a substance in a sample and/or qualifying the type of said substance. Detecting can be accomplished by methods known in the art and those further described herein, including, but not limited to, the direct measurement of the glucosidase enzyme e.g. the sequencing of the gene coding for glucosidase. Any suitable method can be used to detect one or more of the biomarkers described herein. These methods include, without limitation, mass spectrometry (e.g. HPLC-MS/MS), fluorescence (e.g. sandwich immunoassay), HPLC-fluorescence or HPLC-UV preferably after derivatization of free lyso-Gb1.

A biomarker as used herein, preferably is any biological compound, such as a protein and a fragment thereof, a peptide, a polypeptide, a proteoglycan, a glycoprotein, a lipoprotein, a carbohydrate, a lipid, a nucleic acid, an organic or inorganic chemical, a natural polymer, and a small molecule, which is differentially present in a sample from a subject of one phenotypic status (e.g. having a disease) as compared with another phenotypic status (e.g. not having the disease) and which may be isolated from, or measured in the sample from the subject. Furthermore, the biomarker can be the entire intact molecule, or it can be a portion thereof which is preferably detected by mass spectrometric analysis, an antibody, another protein specifically binding the biomarker, functional nucleic acids specifically binding the biomarker and/or a fluorescent label. A biomarker is furthermore considered to be informative if a measurable aspect of the biomarker is associated with a given status of the patient, such as a particular status of Gaucher's disease. Such a measurable aspect may include, for example, the presence, absence, or the level of the biomarker in the sample from the subject and/or its presence as part of a profile of biomarkers. A measurable aspect may also be a ratio of two or more measurable aspects of biomarkers, which biomarkers may or may not be of known identity, for example. A profile of biomarkers comprises at least two such measurable aspects, where the measurable aspects can correspond to the same or different classes of biomarkers such as, for example, a nucleic acid and a carbohydrate. A biomarker profile may also comprise at least three, four, five, 10, 20, 30 or more measurable aspects. In one embodiment, a biomarker profile comprises hundreds, or even thousands, of measurable aspects. In another embodiment, the biomarker profile comprises at least one measurable aspect of at least one biomarker and at least one measurable aspect of at least one internal standard.

In an embodiment of the method according to the present invention an internal standard is added to a sample from a subject. It will be acknowledged that by said addition of internal standard, also referred to herein as IS, to the sample, i.e. spiking of the sample, to be subjected to the method according to the present invention, the concentration of IS in the sample is known and, e.g., by determining the area under the peak, i.e. the peak area, of the internal standard in, e.g., a HPLC-mass spectrometric chromatogram the relation between a peak area and a concentration of a substance, e.g. of IS and/or the biomarker which is in the present case free lyso-Gb1, can thus be calculated, e.g., by calculating the ratio of the peak area of free lyso-Gb1 and the peak area of IS. A person skilled in the art will further acknowledge that various molecules may be used as an IS. Nevertheless an IS having a similar chemical structure compared to the molecule such as the biomarker, e.g. free lyso-Gb1, is preferable. In accordance therewith, the present inventors have in an embodiment chosen lyso-Gb2 which differs from lyso-Gb1 in comprising a further sugar moiety and additionally is not present as such in nature. In a preferred embodiment the molecule being the IS can be distinguished from free lyso-Gb1 in the method of the present invention. In a further preferred embodiment the IS is selected such that a molecule which is ideally not present or rare in nature. In an embodiment of the present invention where the internal standard is added to a sample from a subject, it is preferred that the IS is added such that it is dissolved in a solvent, e.g. ethanol, prior to said addition to the sample. In a further preferred embodiment that the solvent is selected such that said solvent is capable of causing protein precipitation, preferably is capable of causing the protein precipitation step as subject to the method of the present invention.

In some embodiments of the present invention a protein precipitation and/or protein precipitation step is part of the method of the present invention. It will be understood that precipitation as used herein, preferably means the formation of a solid in a solution, i.e. for example the formation of a protein precipitate in a sample, e.g. serum, from a subject. When precipitation, e.g. protein precipitation, occurs in a sample, the solid formed is called the precipitate, or when compacted by a centrifuge, a pellet. The liquid remaining above the solid is in either case called the supernatant. The present invention contemplates different methods of precipitation and/or separating said supernatant and said precipitate or pellet, comprising, among others, settling or sedimentation and centrifugation. A person skilled in the art will know further methods for protein precipitation and/or for separating a supernatant and a protein precipitate, nevertheless said skilled person will acknowledge that if a method, preferably a method of the invention, is applied were precipitated protein will disable a device such as a column or HPLC-column used in connection with the present invention the precipitated protein is preferably separated from the solvent and/or the sample.

In some embodiments of the present invention a level of a biomarker of the present invention, e.g. free lyso-Gb1, determined by a method of the present invention in a sample is compared to a level of the same or another biomarker of the present invention determined by a method of the present invention in another sample, e.g. from the same patient, from another patient, from a control and/or from the same or different time points, and/or a cut-off level, and/or a level of a control and/or a level of an IS. In connection therewith "comparing" or "compared to" as used herein, preferably means the mathematical comparison of the two or more values of the levels of the biomarker(s). It will thus be immediately evident whether one of said values is higher, lower or identical if at least two of such values are compared with each other.

In some embodiments of the present invention the level of the biomarker is also determined in a control. As used herein, a control is preferably a sample from a subject wherein the Gaucher's disease status of said subject is known. In an embodiment a control is a sample of a healthy patient. In a further embodiment an amount of said biomarker is added to said sample of a healthy patient prior to determining the level of said biomarker in said sample of a healthy patient comprising said added biomarker with a method of the present invention. In a further embodiment the control is a sample from at least one subject having a known Gaucher's disease status, such known Gaucher's disease status comprising severe, mild, or healthy Gaucher's disease status, e.g. a control patient. In a further preferred embodiment the control is a sample from a subject not being treated for Gaucher's disease. In a still further preferred embodiment the control is a sample from a single subject or a pool of samples from different subjects and/or samples taken from the subject(s) at different time points.

The term "level" or "level of a biomarker" as used herein, preferably means the concentration of a substance, preferably of a biomarker of the invention and more preferably of free lyso-Gb1, within a sample or a subject. It will be understood by a skilled person that in certain embodiments said sample is not necessarily subjected to a method of the invention as a non-processed sample, the method comprising determining a level of said biomarker, i.e. said sample may be subjected, e.g. to a step of protein precipitation, separation, e.g. centrifugation and/or HPLC and subsequently subjected to a step of determining the level of the biomarker, e.g. using mass spectrometric analysis. It should be further noted that whenever the term "a" level of a biomarker is used in connection with a level of the biomarker of the invention which is to be determined according to the present invention, "the" level of the biomarker of the present invention which is to be determined by the methods of to the present invention and which is contained in the sample subjected to the method(s) of the invention is meant.

The level of a biomarker is different between different statuses of Gaucher's disease, if the mean or median level of the biomarker in the different groups is calculated to be statistically significant. Common tests for statistical significance include, among others, t-test, ANOVA, Wilcoxon, Mann-Whitney, odds ratio and Kruskal-Wallis. Biomarkers, alone or in combination, provide measures of relative risk that a subject belongs to one phenotypic status or another. Therefore, biomarkers of the present invention are useful in an embodiment of the present invention as markers for disease, therapeutic effectiveness of a drug or a treatment.

The term "determining the level" of a biomarker as used herein, preferably means methods which include quantifying an amount of at least one substance in a sample from a subject and/or quantifying an amount of said substance contained in a part of the body of the subject, such as saliva, blood, lymph, serum, plasma or liquor and/or quantifying an amount of said substance in the subject, the substance being selected from the group comprising a biomarker.

It will be understood by a person skilled in the art that detecting and/or determining the level of free lyso-Gb1 in a sample from the subject, thus preferably comprises that Gb1 present in the blood of a subject is not chemically converted, transformed or derivatized such that free lyso-Gb1 cannot be detected and/or the level thereof cannot be determined separate from and/or apart from Gb1. The person skilled in the art will acknowledge that Gb1 present in a sample from a subject which is subjected to a step of deacetylation, e.g. by hydrolysis in methanolic sodium hydroxide, will result in cleavage of the fatty acid moiety from the Gb1 and thus will undesirably result in a chemically converted, transformed or derivatized form of Gb1 which cannot be differentiated from free lyso-Gb1. It is thus the merit of the present inventors to recognize that free lyso-Gb1 apart from Gb1 is useful in a method for diagnosing Gaucher's disease.

In a preferred embodiment of the methods of the present invention the method is for detecting and/or determining the level of free lyso-Gb1 in a sample from a subject, wherein Gb1 present in the sample from the subject is not subjected to a step resulting in deacetylation of Gb1, preferably is not subjected to a step resulting in cleavage off of a fatty acid moiety from the Gb1 contained in the sample. In a further preferred embodiment of the method of the present invention Gb1 present in the sample from the subject is not chemically converted, transformed or derivatized. In a still further preferred embodiment of the method of the present invention free lyso-Gb1 present in the sample from the subject is separated from Gb1 present in the sample from the subject prior to a step that would result in cleavage of a fatty acid moiety from the Gb1 and/or prior to a step in which Gb1 is chemically converted, transformed or derivatized. In a still further preferred embodiment a step of detecting and/or determining the level of a biomarker in a sample from the subject, wherein the biomarker is free lyso-Gb1, is performed subsequent to separation using HPLC by application of mass spectrometric analysis.

A subject is considered to be a healthy subject with regard to Gaucher's disease, if the subject does not suffer from symptoms associated with Gaucher's disease. Moreover in an embodiment of the methods of the invention a subject will be considered to be healthy if it has no mutation of the functional parts of the cerebrosidase gene and/or no mutation of the cerebrosidase gene resulting in a reduction of or deficiency of the enzyme glucocerebrosidase or the activity thereof, resulting in symptoms associated with Gaucher's disease. Said mutations will be detected if a sample from the subject is subjected to a genetic testing for such mutations as described herein. In a further embodiment of the present invention a sample from a healthy subject is used as a control sample or as a blank matrix in the methods of the present invention. A blank matrix as referred to herein, is preferably a sample from a healthy subject. Nevertheless it will be understood that such a blank matrix may contain a native level of free lyso-Gb1.

In an embodiment of the present invention the level of a biomarker is indicative for the subject for suffering from or for being at risk for developing a disease or disorder. The level of the biomarker determined by the method according to the present invention is compared to a control level of the biomarker, wherein the result of said comparison allows for diagnosing a disease.

More specifically, comparing the level of the biomarker in the sample from the subject to the control level of the biomarker comprises comparing the level of the biomarker in the sample from the subject to a cut-off level, wherein if a level of the biomarker in the sample from the subject is elevated, increased or higher compared to the cut-off level, this is indicative that the subject is suffering from or is at risk for developing Gaucher's disease and/or, wherein if a level of the biomarker in the sample from the subject is decreased or lower compared to the cut-off level this is indicative that the subject is not suffering from or is not at risk for developing Gaucher's disease. It is also within the present invention that comparing the level of the biomarker in the sample from the subject to a control level allows for determining the severity of Gaucher's disease, wherein if a level of the biomarker in the sample from the subject is elevated, increased or higher compared to the control level that is indicative that the subject is suffering from or is at risk for developing Gaucher's disease of a more severe status or progression; and wherein if a level of the biomarker in the sample from the subject is decreased or lower compared to the control level that is indicative that the subject is suffering from or is at risk for developing Gaucher's disease of a less severe status or progression. In a further embodiment of the present invention that comparing the level of the biomarker in the sample from the subject to the control level comprises comparing a level of the biomarker in said subject to a level of the biomarker detected in a sample from a control, wherein if a level of the biomarker in the sample from the subject is elevated, increased or higher compared to the control sample this is indicative that the subject is suffering from and/or is at risk for developing Gaucher's disease; and/or a level of the biomarker in the sample from the subject is elevated, increased or higher compared to the control sample this is indicative that the subject is suffering from or is at risk for developing Gaucher's disease of a more severe status or progression. Said control preferably is selected from the group comprising healthy subjects, subjects suffering from Gaucher's disease or being at risk of suffering from Gaucher's disease symptoms, subjects being positively tested for a mutation or a combination of mutations of the cerebrosidase gene, wherein the mutation or the combination of mutations of the cerebrosidase gene are indicative for a perspective of the subject to develop Gaucher's disease of a more severe or less severe status or progression. In a further embodiment of the present invention that a control level is determined in a sample from a control, wherein optionally free lyso-Gb1 is added to the sample from the control in a specific quantity prior to determining the level of free lyso-Gb1 in the sample from the control.

It is the merit of the present inventors that a method for diagnosing Gaucher's disease in a subject could be established wherein the method comprises detecting a biomarker in a sample from a subject, wherein the biomarker is free lyso-Gb1, preferably further comprising determining a level of the biomarker in the sample from the subject, and more preferably further comprising comparing the level of the biomarker in the sample from the subject to a cut-off level, which shows high sensitivity, i.e. a sensitivity of at least 99.0%, 99.1%, 99.2%, 99.3%, 99.4%, 99.5%, 99.6%, 99.7%, 99.8%, 99.9% or 100% and high specificity of at least 99.0%, 99.1%, 99.2%, 99.3%, 99.4%, 99.5%, 99.6%, 99.7%, 99.8%, 99.9% or 100%. In a further embodiment of the present invention that the methods according to the present invention allow for diagnosing Gaucher's disease in a subject independent from a progression status of Gaucher's disease in the subject. More specifically, the methods of the present invention allow for diagnosing Gaucher's disease in a subject having an early status of Gaucher's disease as well as in a subject having an advanced or progressed status of Gaucher's disease.

The power of a method to correctly diagnose Gaucher's disease, is commonly measured as the sensitivity of the method, the specificity of the method or the area under a receiver operated characteristic curve (also referred to herein as "ROC curve"). An ROC curve is a plot of the true positive rate against the false positive rate for the different possible cut-off levels of a diagnostic method. An ROC curve shows the relationship between sensitivity and specificity. Sensitivity is the percentage of true positives that are predicted by a test to be positive, while specificity is the percentage of true negatives that are predicted by a test to be negative. An ROC-curve provides the sensitivity of a test as a function of 1-specificity. The greater the area under the ROC-curve the more powerful the predictive value of the test. Accordingly, an increase in sensitivity will be accompanied by a decrease in specificity. The closer the curve follows the left axis and then the top edge of the ROC space, the more accurate the test. Conversely, the closer the curve comes to the 45-degree diagonal of the ROC graph, the less accurate the test. Therefore, the area under the ROC is a measure of test accuracy. The accuracy of the test depends on how well the test separates the group being tested into those with and without the disease in question. An area under the curve (also referred to herein as "AUC") of 1 represents a perfect method, while an area of 0.5 represents a less useful method. Thus, preferred diagnostic methods of the present invention have an AUC greater then 0.50, more preferred methods have an AUC greater than 0.9 and most preferred methods have an AUC greater than 0.998.

Other useful and suitable measures for the utility of a method are positive predictive value and negative predictive value. A positive predictive value is the percentage of actual positives that test as positive. A negative predictive value is the percentage of actual negatives that test as negative.

Methods for qualifying Gaucher's disease status in a subject that use biomarkers of the prior art, e.g. chitotriosidase and/or CCL18 show a sensitivity and specificity typically not more than 90%.

A person skilled in the art will acknowledge that although the specificity and the sensitivity of the methods according to the present invention are as high as described above and were determined as described in the Examples hereinafter, individual cases may not be excluded where a patient having Gaucher's disease will be tested false negative or where a patient not having Gaucher's disease will be tested false positive with a method of the invention. Taking said cases into account while determining the specificity and the sensitivity of the method according to the present invention, the specificity and the sensitivity will be lower than the above described values. Nevertheless, the person skilled in the art will also acknowledge that such high specificity and such high sensitivity as has been outlined above has never been described before for a method for diagnosing Gaucher's disease. Therefore it is important to note that although the sensitivity and the specificity of the method of the present invention may vary if patient collectives other than the one reported in the Example part, e.g. varying in number of patients, will are subject to the methods of the present invention, it is the firm belief of the inventors that no method known in the prior art using biomarkers will achieve a higher specificity and a higher sensitivity compared to the methods according to the present invention. This is especially true since the limit of detection of the methods of the present invention allows for determining the level of free lyso-Gb1 in many healthy subjects. Accordingly, a diseased subject tested false negative applying the methods of the present invention is tested false negative for the reason that a level of the biomarker in a sample from said false negative tested diseased subject is as high as the level of the biomarker in a sample from a healthy subject. In particular it is important to note that said false negative tested subject is not tested negative for the reason that the level of the biomarker was too low to be determined by the method of the present invention.

A "limit of detection" of a substance such as free lyso-Gb1, as used herein, preferably is a level of the substance determined by a method for determining a level of the substance, wherein a level less then or lower then said limit of detection cannot be determined by said method. It is thus immediately clear that a "cut-off level" and a "limit of detection", as used herein, are preferably not necessarily identical, although both reflect a certain level of a substance, e.g. of a biomarker of the present invention. It will be immediately understood that in contrast to a cut-off level will be selected preferably such that selectivity and sensitivity of the method are as high as possible. In contrast thereto a limit of detection represents an absolute level of the biomarker of the present invention which reflects the minimum level of biomarker which can be detected with a method for determining the level of said biomarker. It is thus immediately clear that a limit of detection depends on the method for determining a level of a substance and on the substance the level of which is to be determined by the method. A skilled person will immediately understand that a high limit of detection, e.g. higher than an ideal cut-off level would possibly result in a low sensitivity of the method since the percentage of true positives that are predicted by a test to be positive also depends on whether a level of the biomarker may be determined for said true positives. In other words, if the limit of detection is higher than an ideal cut-off level, true positives having a level of the biomarker slightly higher than the cut-off level may not be distinguished from true negatives having a level of the biomarker lower than the cut-off level since no level of the biomarker may be determined for both true positives having a level of the biomarker slightly higher than the cut-off level and negatives having a level of the biomarker lower than the cut-off level. It is thus immediately clear that a low limit of detection is of advantage. It is therefore also the merit of the inventors to show that a lower limit of detection allows for a method for diagnosing Gaucher's disease in a subject comprising a step of determining a level of a biomarker present in the sample with higher selectivity and sensitivity.

An "ideal cut-off level" as used herein, preferably is the cut-off level as described herein the method using said ideal cut-off level has the highest selectivity and sensitivity.

It is an embodiment of the methods according to the present invention to comprise a step of validating said method by diagnosing a disease or disorder, preferably Gaucher's disease in a subject by the method of the present invention; a step of diagnosing the disease or disorder, preferably Gaucher's disease, in a subject by a genetic testing, comprising sequencing of a gene, preferably sequencing of a gene a mutation of which is known to the one skilled in the art to cause the disease or disorder, more preferably sequencing the cerebrosidase gene in case of Gaucher's disease; and comparing the results of said method and said genetic testing. A healthy subject as used herein, preferably is considered to be healthy with regard to a disease or disorder if said subject is not suffering from symptoms associated with said disease or disorder and if the result of a genetic testing reveals no mutations of a gene a mutation of which is known to the one skilled in the art to cause the disease or disorder. A healthy subject also is understood to be a subject being positively tested for not having Gaucher's disease.

The term "qualifying Gaucher's disease status" in a subject as used herein, preferably means a classification of a subject's biomarker profile selected from the group comprising to identify or detect the presence or absence of Gaucher's disease in the subject, to predict the onset of or the risk for developing of Gaucher's disease in the subject, to determine the course of Gaucher's disease in a subject, to determine and/or predict the severity of Gaucher's disease in a subject, to determine whether a subject suffers from an early status of Gaucher's disease or an advanced or progressed status of Gaucher's disease or to determine whether a level of a biomarker in a subject has significantly changed over time.

The term "managing subject treatment" or "subject management" as used herein, preferably refers to the behavior of the clinician or physician subsequent to the determination of Gaucher's disease status. For example, if the result of the method according to the present invention is inconclusive or there is reason that confirmation of status is necessary, the physician may order new tests, such as testing for the function of the glucocerebrosidase and/or sequencing of the gene coding for the glucocerebrosidase. Alternatively, if the status indicates that treating for Gaucher's disease is appropriate, the physician may schedule the subject for treating for Gaucher's disease. Likewise, if the status is negative or if the results show that treatment has been successful, no further management may be necessary. Nevertheless a person skilled in the art will immediately acknowledge that besides gene therapy any therapy applied, e.g. ERT and/or SRT has to be applied lifelong to a Gaucher's disease patient. Furthermore it is an embodiment of the present invention that managing subject treatment comprises titrating of a dose of a drug applied as a treatment for Gaucher's disease, e.g. units of recombinant enzyme applied in ERT, administered to a patient. In some embodiments of the methods of the present invention wherein a level of a biomarker present in a sample from a subject is determined at several points in time, or is compared to other levels of the biomarker, a cut-off level and/or a level of said biomarker in a control, a skilled person will apply or not apply a therapy, or amend a therapy already applied in order to treat or not to treat, or to continue treating Gaucher's disease.

It is within the present invention that a skilled person will apply a dosage and/or maintain a dosage or amend a dosage, e.g. apply a dosage or a higher dosage, i.e. elevate a dosage, if such a comparison of the level of a biomarker shows e.g. that the level of said biomarker is higher than for example, a cut-off level, i.e. the patient is diagnosed to have Gaucher's disease; or that a level determined in the same patient earlier in time is lower or the same, i.e. a therapy applied is not sufficient, i.e. does not result in a decrease in the level. On the other hand skilled person will apply or not apply a dosage or maintain or reduce a dosage, e.g. apply no dosage or a lower dosage, i.e. decrease a dosage, if such a comparison of the level of a biomarker shows e.g. that the level of said biomarker is lower than for example, a cut-off level, i.e. the patient is diagnosed not to have Gaucher's disease; or that a level determined in the same patient earlier in time is higher, i.e. a therapy applied is sufficient, i.e. does result in a decrease in the level. In an embodiment of the present invention a relatively high level of free lyso-Gb1 based on such a comparison is indicative for applying a high dosage of recombinant enzyme applied in ERT and/or a relatively low level of free lyso-Gb1 based on such a comparison is indicative for applying a low dosage of recombinant enzyme applied in ERT. Nevertheless it will also be immediately understood that a skilled person will consider a patient's history, i.e. a skilled person managing subject treatment of a patient suffering from Gaucher's disease and being treated such that a level of biomarker is lower than a cut-off level, for example, will not decide to stop treatment rather than decrease a dosage and increase the time between further applications of the methods of the present invention.

The course of Gaucher's disease may be determined by the method according to the present invention by determining a level of the biomarker in the sample from the subject at different time points in the course of the disease. It is important to note that a single application of a method for diagnosing Gaucher's disease according to the present invention allows for diagnosing Gaucher's disease and in certain embodiments comprises a step of managing subject treatment based on the diagnosis of whether the subject is suffering from or for being at risk for developing Gaucher's disease. If a subject a sample of which is thus subjected to the method of the present invention is tested positive for suffering from or to be at risk for developing Gaucher's disease a skilled clinician will know how to decide concerning managing subject treatment, i.e. how the subject will be treated, e.g. applying a certain dose of enzyme in relation to an ERT. It will be immediately understood that independent of the decision of a skilled clinician on how to manage subject treatment the skilled clinician may decide for at least one additional application of the method according to the present invention on a later time point. It is thus an embodiment of the present invention that the levels of the biomarker determined at the different time points, wherein different time points means at least two time points, may be compared. Without wishing to be bound by any theory the present inventors have found that the level of the biomarker of the present invention in samples form one particular patient may be correlated to the severity of the disease in said patient at the time point the sample from the patient is taken. It will be thus immediately understood that an elevated level of the biomarker determined in the sample of a later time point compared to the level of the biomarker determined in the sample of an earlier time point is indicative for a more severe status of the subject at the later time point compared to the status of the subject at the earlier time point. A decreased level of the biomarker determined in the sample of a later time point compared to the level of the biomarker determined in the sample of an earlier time point is indicative for a less severe status of the subject at the later time point compared to the status of the subject at the earlier time point. Accordingly, in one aspect the present invention provides a method for determining the course of Gaucher's disease in a subject comprising the step of determining at several points in time a level of a biomarker present in a sample from the subject, wherein the biomarker is free lyso-Gb1. In a further aspect the invention concerns a method for determining the effectiveness of at least one treatment applied to a subject being positively tested for suffering from or being at risk for developing Gaucher's disease comprising the step of determining at several points in time a level of a biomarker present in a sample from the subject, wherein the biomarker is free lyso-Gb1. It will be immediately understood by a person skilled in the art that the methods of the present invention thus allow for selecting a therapy and/or adjusting the doses and/or dosage of a selected therapy based on the results of the method of the invention. If for example the subject is scheduled for treating for Gaucher's disease the method for diagnosing Gaucher's disease in a subject according to the present invention may be applied every 3 months and levels of the biomarker thus determined will be compared in order to determine the effectiveness of the treatment(s) and/or therapy/therapies applied to the subject. If the subject reaches a status, wherein a stable level of the biomarker is maintained over time the frequency of application of the method for diagnosing Gaucher's disease in a subject according to the present invention may be reduced to every 6 month. If the dosage of the therapy is changed, e.g. the units of recombinant enzyme applied in ERT are reduced or increased, the frequency of application of the method for diagnosing Gaucher's disease in a subject according to the present invention may be set back to every 3 month. By comparison of the determined levels of the biomarker in the samples from the subject the skilled physician will recognize whether the level of the biomarker increases, decreases or whether a stable level of the biomarker is maintained over time. Accordingly, the skilled physician may decide to reduce the dosage of the therapy, e.g. the units of recombinant enzyme applied in ERT; to increase the dosage of the therapy; or to maintain the dosage of the therapy according to the comparison of the levels of the biomarker determined with the method according to the present invention. A reduction of about 60% of the level of free lyso-Gb1 within a period of 12 month is indicative for a successful therapy for Gaucher's disease, wherein reduction as used herein, preferably means that the level of free lyso-Gb1 determined by the method of the present invention determined at the end of a time period is compared to the level of free lyso-Gb1 determined by the method of the present invention determined at the beginning of said time period. Accordingly the skilled physician may decide to reduce the dosage of the applied therapy or to maintain the dosage of the therapy. If the reduction of the level of free lyso-Gb1 is significantly weaker the skilled physician may decide to increase the dosage of the therapy. It is also a merit of the present inventors to have recognized that the reduction of the level of free lyso-Gb1 correlates with the effectiveness of a therapy. The stronger the reduction of the level of the free lyso-Gb1 within a time period, e.g. 12 months, the more successful is a therapy, such as for example ERT, SRT or a chaperone based therapy. It is thus a further embodiment of the present invention that the method of the present invention is for comparing the effectiveness of a therapy or of at least two therapies applied to a subject.

A person skilled in the art thus will acknowledge that the progression, i.e. course of Gaucher's disease, as well as the effectiveness of a therapy in a single subject can be monitored by frequent determining of the level of free lyso-Gb1 in samples from the subject.

In a further aspect the invention concerns a method for determining the effectiveness of at least one treatment applied to a subject being positively tested for suffering from or being at risk for developing Gaucher's disease comprising the step of determining at several points in time a level of a biomarker present in a sample from the subject, wherein the biomarker is free lyso-Gb1. In connection with what has been outlined above in relation to managing subject treatment a person skilled in the art will immediately understand that the effectiveness of one treatment or the combination of at least two treatments may be compared applying the methods of the present invention. Thus it is possible to test and compare several new drugs, dosage forms, dosages or treatments for Gaucher's disease by the method of the present invention.

It is an embodiment of the present invention that the method for diagnosing Gaucher's disease according to the present invention is independent of whether the subject has or has not been previously treated for Gaucher's disease. Thus the sample from the subject may be a sample from a subject who has been previously treated for Gaucher's disease as well as a sample from a subject who has not been previously treated for Gaucher's disease. It is thus a further embodiment of the present invention that the method of the present invention comprises a step of managing subject treatment and/or determining a level of the biomarker in the sample from the subject after subject management. Said subject treatment can be based on the diagnosis of whether the subject is suffering from or for being at risk for developing Gaucher's disease; on the detection of the biomarker in a sample from the subject after subject management; or on the determining of the level of the biomarker in the sample from the subject after subject management. Nevertheless a person skilled in the art will understand that a sample of some patients not having Gaucher's disease or of some patients being successfully treated for Gaucher's disease will show a level of free lyso-Gb1 lower than the limit of detection.

Without wishing to be bound by any theory the present inventors assume that the level of free lyso-Gb1 present in a sample from a subject further correlates with the severity of the disease in a subject suffering from Gaucher's disease. In connection therewith the present inventors found by evaluating the results provided herein (e.g. shown in FIG. 4 herein) that although, in principle, the level of free lyso-Gb1 is different in particular individuals, and more specifically may be different in particular individuals having the same mutation(s), that the higher is a level of free lyso-Gb1, the higher is the severity of a course of Gaucher's disease in terms of a statistical mean according to a clinical score. Thereby the level of free lyso-Gb1 correlates with the severity of Gaucher's disease in that in patients being positively tested for distinct mutations of the glucocerebrosidase gene being known to generally causes a mild (e.g. N370S mutation) or a more severe (e.g. L444P mutation) course of Gaucher's disease, a level of free lyso-Gb1 determined in said patients statistically correlated with the severity generally related to such mutation.

Thus a further embodiment of the different aspects of the present invention concerns a method for determining the severity of Gaucher's disease in a subject comprising a step of a) determining a level of the biomarker present in a sample from the subject wherein the biomarker is free lyso-Gb1 and a step of
b) determining the severity of Gaucher's disease, e.g. by comparing the level of free lyso-Gb1 in a subject preferably determined by a method of the present invention to a clinical score.

In connection therewith it is important to note that if a level of free lyso-Gb1 is determined in samples from the patients suffering from Gaucher's disease showing the L444P mutation upon sequencing of the cerebrosidase gene (homozygous and compound heterozygous) subjected to a method of the present invention a mean-level of free lyso-Gb1 is higher than the mean-level of the free lyso-Gb1 determined in samples from the patients suffering from Gaucher's disease showing the N370S mutation upon sequencing of the cerebrosidase gene, applying the same method (FIG. 4). Mutation L444P is known to cause a more severe course of Gaucher's disease—this is especially true in case the subject is homozygous as to said mutation. Corresponding to that a higher mean-level of free lyso-Gb1 is determined in the homozygous compared to the homozygous N370S mutation (194 ng/ml and 159 ng/ml, respectively, see FIG. 4). Moreover patients having a compound heterozygous L444P mutation have a significant lower free lyso-Gb1 level than homozygous ones (89 ng/ml and 45.4 ng/ml, respectively). A person skilled in the art will know clinical scores to categorize the severity of Gaucher's disease or symptoms or an entirety of symptoms thereof. It is thus an embodiment of the method of the present invention that the course of Gaucher's disease in a patient is predicted and more particularly the severity of Gaucher's disease is determined based on the level of the biomarker determined according to the method of the present invention.

It is an embodiment of the present invention that levels of chitotriosidase determined in patients not having a mutation of the chitotriosidase gene, in particular not having a 24-bp duplication as described herein, serve as a basis for correlating the severity of Gaucher's disease in that a mean-level of chitotriosidase determined in a sample from said patients as described herein is correlated to a severity of Gaucher's disease. Thus, for example a level of chitotriosidase below 200 nmolMU/h/ml is correlated with a Gaucher's disease status of a patient not suffering from Gaucher's disease. In connection therewith it is important to note that a patient treated for Gaucher's disease may also exhibit a level of chitotriosidase below 200 nmolMU/h/ml. A level of more than 2000 nmolMU/h/ml is correlated to a "fullblown" or "severe" Gaucher's disease status and a level of chitotriosidase from 200 to 2000 nmolMU/h/ml is correlated to a "mild" Gaucher's disease status.

In connection therewith is important to note that a level of chitotriosidase from 200 to 1000 nmolMU/h/ml may also be found in a sample from a subject suffering from another LSD such as Niemann-Pick type C or Krabbe's disease, thereby rendering the use of chitotriosidase for diagnosing Gaucher's disease unsuitable. Therefore, the considerations outlined above in connection with the use of a level of chitotriosidase for correlation with the severity of Gaucher's disease typically apply only for patients wherein the presence or absence of Gaucher's disease and/or other LSD known to show elevated levels of chitotriosidase was proven by mutational analysis.

If a level of free lyso-Gb1 is determined according to the methods of the present invention in said patients not having a mutation of the chitotriosidase gene, in particular not having a 24-bp duplication as described herein, said level of free lyso-Gb1 determined in a sample from each of said patients is correlated to the chitotriosidase level of said patients and/or to the grade of severity of Gaucher's disease and/or status of Gaucher's disease of said patient. Thus a grade of severity of Gaucher's disease and/or status of Gaucher's disease, comprising healthy, mild and severe is determined and more preferably is correlated to levels of chitotriosidase and/or ranges of levels of chitotriosidase as outlined above.

A person skilled in the art will acknowledge that a level of the biomarker of the present invention determined in a sample from a subject wherein said level of the biomarker is correlated with the severity of Gaucher's disease as described above, will be indicative for applying a certain therapy and/or dose or dosage of said therapy. For example, if the level of the biomarker in determined according to the methods of the invention is correlated with "severe" or "fullblown" Gaucher's disease status the subject is scheduled for treatment of Gaucher's disease and the method for diagnosing Gaucher's disease in a subject according to the present invention may be applied every 3 months and levels of the biomarker thus determined will be compared in order to determine the effectiveness of the treatment(s) and/or therapy/therapies applied to the subject. If the subject reaches a status, wherein the level of the biomarker is correlated with a "mild" Gaucher's disease or wherein a stable level of the biomarker is maintained over time the frequency of application of the method for diagnosing Gaucher's disease in a subject according to the present invention may be reduced to every 6 month.

In another aspect the present invention is related to a method of determining the effectiveness of a composition for the treatment of Gaucher's disease. Such method may comprise the steps of determining a level of free lyso-Gb1 in a subject having Gaucher's disease; administering to said subject said compound in an amount sufficient to determine the effectiveness of said compound; re-determining the level of free lyso-Gb1 in said subject; comparing the level of free lyso-Gb1 determined before and after administering said composition, wherein a lower level of free lyso-Gb1 determined after administering said composition compared to the level of free lyso-Gb1 determined after administering said composition indicates the effectiveness of said compound for treating Gaucher's disease.

The present invention is now further illustrated by the following figures and examples from which further features, embodiments and advantages may be taken.

More specifically,

FIG. 1A is a boxplot indicating levels of free lyso-Gb1 in ng/ml plasma;

FIG. 1B is a boxplot indicating levels of free lyso-Gb1 in ng/ml plasma grouped by gender of the subjects;

FIG. 2A is a graph showing receiver operating characteristics (ROC) curves of free lyso-Gb1 and chitotriosidase;

FIG. 2B is a graph showing receiver operating characteristics (ROC) curves of free lyso-Gb1 and CCL18;

FIG. 3A is a diagram showing free lyso-Gb1 in ng/ml plasma as a function over time for a total of 20 German Gaucher's disease patients;

FIG. 3B is a diagram showing free lyso-Gb1 in ng/ml plasma as a function over time for a total of 24 non-treated Gaucher's disease patients (10 German, 14 Israeli patients);

FIG. 3C is a diagram showing free lyso-Gb1 in ng/ml plasma as a function over time for a total of 9 Israeli Gaucher's disease patients before and after start of therapy;

FIG. 3D is a diagram showing regression based values of free lyso-Gb1 in ng/ml plasma as a function over time for Israeli and German Gaucher's disease patients before and after start of therapy;

FIG. 4 is a table showing the median level of free lyso-Gb1 for two frequent mutations;

FIG. 5A is an HPLC-mass spectrometric chromatogram displaying peak intensity of free lyso-Gb1 and IS of a healthy subject;

FIG. 5B is an HPLC-mass spectrometric chromatogram displaying peak intensity of free lyso-Gb1 and IS of a Gaucher's disease patient;

FIG. 5C is an HPLC-mass spectrometric chromatogram displaying peak intensity of free lyso-Gb1 and IS of a Gaucher's disease patient;

BRIEF DESCRIPTION OF THE FIGURES

FIG. 3B is a diagram showing free lyso-Gb1 as a function over time determined by the method according to the present invention in ng/ml of plasma of a total of 24 non-treated Gaucher's disease patients (10 German, 14 Israeli patients); Non-treated as used herein, preferably means that no treatment, e.g. enzyme replacement therapy, has been applied with regard to Gaucher's disease. For the analysis of the change of the level of free lyso-Gb1 over time in Gaucher's disease patients as described in Example 3 non aggregated data was used for those patients for which more than one blood sample has been analysed.

FIG. 4 is a table showing the median level of free lyso-Gb1 in patients positively tested for one of two frequent mutations of the glucocerebrosidase gene, namely N370S and L444P in the homozygous as well as in the compound heterozygous situation, wherein compound heterozygosity is the condition of having two heterogeneous recessive alleles at a particular locus that can cause genetic disease in a heterozygous state. A person skilled in the art will acknowledge that patients having a mutation L444P of the glucocerebrosidase gene also face a more malignant prognosis, which is particularly true in the homozygous situation. Accordingly, it is an embodiment of the present invention that the method according to the present invention comprises determining the severity of Gaucher's disease. Said determining the severity of Gaucher's disease comprises determining a level of the biomarker, preferably free lyso-Gb1, present in the sample from the subject and/or comparing said level of said biomarker determined in samples from subjects having different mutations of the glucocerebrosidase gene and/or having no mutation of the glucocerebrosidase gene. The present inventors have found that in a sample from a patient being positively tested for having a homozygous L444P mutation of the cerebrosidase gene the level of free lyso-Gb1 determined by the method according to the present invention is about 194 ng/ml and is elevated compared to the level of free lyso-Gb1 determined in a sample from a patient being positively tested for having a homozygous N370S mutation of the cerebrosidase gene, wherein the level of free lyso-Gb1 determined by the method according to the present invention is about 159 ng/ml). The inventors have also found that in a sample from a patient being positively tested for having a compound heterozygous L444P mutation the level of free lyso-Gb1 determined by the method according to the present invention is 89 ng/ml and is significantly lower compared to the level of free lyso-Gb1 determined by the method according to the present invention in a sample from a patient being positively tested for having a homozygous L444P mutation wherein the level of free lyso-Gb1 determined by the method according to the present invention is about 45.4 ng/ml. Without wishing to be bound by theory the present inventors believe that the level of free lyso-Gb1 in a sample from a subject determined by a method of the present invention is indicative for the severity of Gaucher's disease. It is thus a further embodiment of the present invention that the method of the present invention is for determining the effectiveness of at least one treatment applied to a subject being positively tested for suffering from and/or being at risk for developing Gaucher's disease. The numbers depicted in brackets indicate the ranges of concentration measured in the respective patient group. IQR means interquartile range. All patients that were subjected to a therapy for Gaucher's disease were subjected to ERT.

EXAMPLES

Figure 1A:
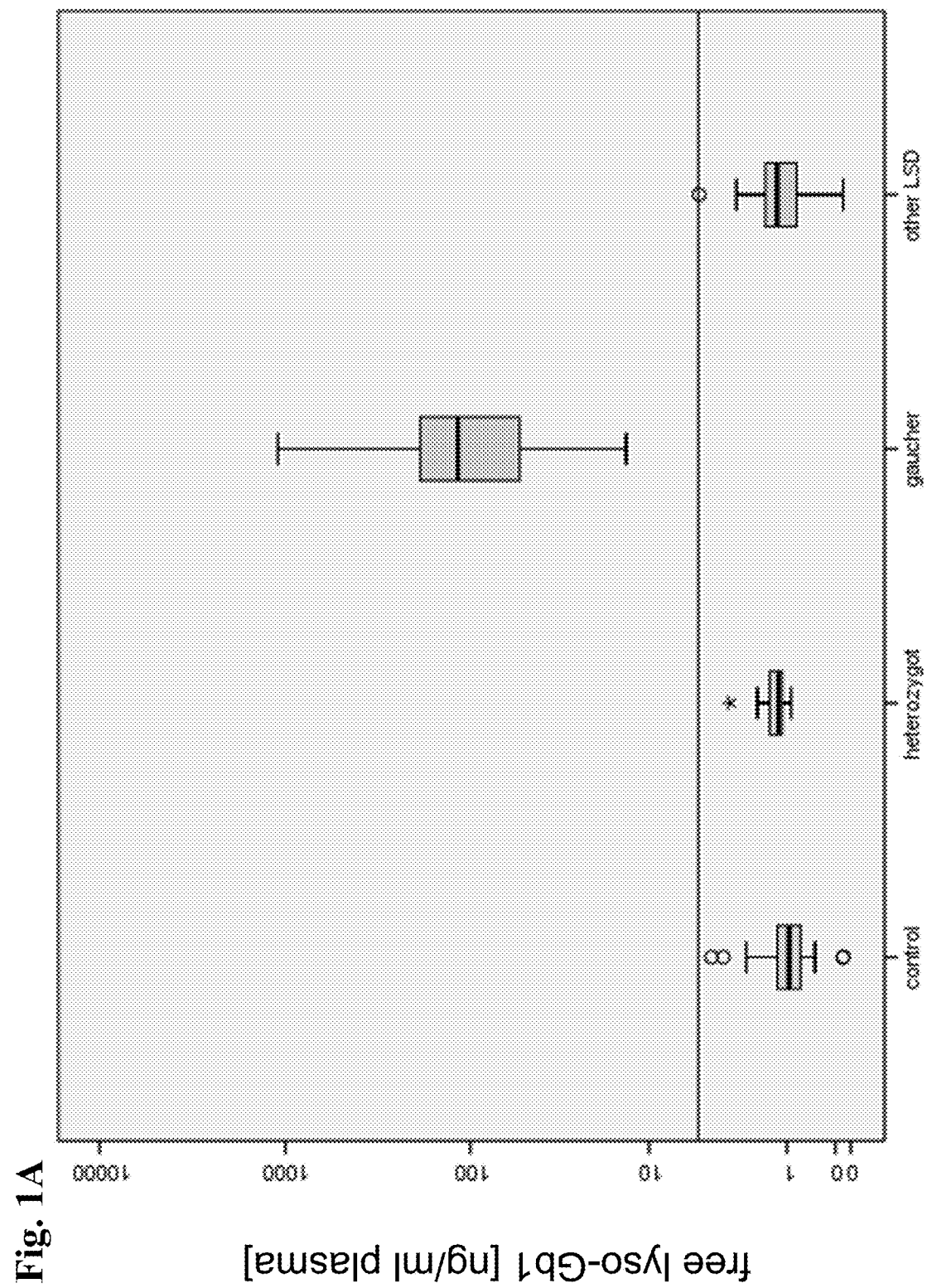
FIG. 1A is a boxplot indicating levels of free lyso-Gb1; the y-axis demonstrates the logarithmised levels of free lyso-Gb1 in ng/ml determined in plasma of Patients by the method according to the present invention, wherein the x-axis depicts groups of patients, which have been grouped as described in Example 2. The boxplot represents the $25^{th}$ and $75^{th}$ percentile of each group of patients by the bottom and top of the box, respectively; the band near the middle of the box represents the $50^{th}$ percentile (i.e. the median) of each group; The whiskers represent one standard deviation above and below the mean of the data; Any data not included between the whiskers is shown as an outlier with a small circle or star. The horizontal line represents the cut-off level of 5 ng/ml.

In the Examples described in the following human plasma was used as a sample from a subject. Nevertheless a person skilled in the art will acknowledge that depending on the used type of sample from a subject, e.g. comprising saliva, liquor, plasma, serum, full blood, blood on a dry blood filter card or another blood product, the method of the present invention has to be adjusted to the type of sample and furthermore a cut-off level has to be determined for each type of sample according to the method described in the following examples. The present inventors have found that using a sample of human serum in the method as described below instead of a sample of human plasma will lead to identical results according to a detection of and a thus determined level of free lyso-Gb1, if the sample of human serum and the sample of human plasma derive from the same subject, and were taken at the same time point; and wherein the samples were measured in parallel; and, more particularly, will lead to the same cut-off level. Without whishing it be bound and in way of illustrative examples, by use of saliva from a human patient a method may be adjusted in dependence of a pH value of the sample; or a cut-off level may be determined being 20 ng/ml if using full blood or blood collected on a dry blood filter card as a sample from a subject.

Example 1: Method for the Detection of Free Lyso-Gb1 in Human Serum

Equipment

For detecting free lysoGb-1 in a sample of plasma from a subject the following equipment was used.

| Apparatus/Piece of Equipment | Type/Producer |
|---|---|
| HPLC pump | Series 200, Perkin Elmer, USA |
| Sample injector | Series 200, Perkin Elmer, USA |
| Column oven | Series 200, Perkin Elmer, USA |
| Mass selective detector | API 4000 Q TRAP, AB SCIEX, USA/Canada |

| Apparatus/Piece of Equipment | Type/Producer |
|---|---|
| Multi-tube vortexer DVX-2500 | Henry Troemner LLC, USA |
| Vortex mixer | Vortex Genie 2; Scientific Industries, USA |
| Centrifuge | Megafuge 1.0; Heraeus, Germany |
| Multipette(s), pipette(s) | Eppendorf, Germany |
| Water bath | SW21-C, Julabo, Germany |

Reagents

For detecting free lysoGb-1 in a sample of plasma from a subject the following reagents were used.

To that extent that values depend on temperature (e.g. the pH value) such values were determined at a temperature of 25° C.

| Reagent | Purity |
|---|---|
| Acetonitrile (ACN) | HPLC-grade or Gradient grade |
| Acetone | 99.5% |
| Dimethylsulfoxide (DMSO) | HPLC grade |
| Ethanol (EtOH) | p.a., 96% |
| Formic acid (FA) | p.a., 98-100% |
| Methanol (MeOH) | Gradient (LiChrosolv) |
| Trifluoroacetic acid (TFA) | purum > 98% |
| Water | ASTM-I |

The abbreviation "p.a." as used herein means "pro analysis".

The term "purum" as used herein, preferably means a commercial grade of a chemical compound having a purity of the above specified value.

ASTM-I as used herein refers to a water grade standard purity achieved by purification methods comprising Reverse Osmosis and Ultraviolet (UV) Oxidation.

Preparation of Calibration Standards

A Lyso-Gb1 stock solution was prepared dissolving 1.70 mg Lyso-Gb1 (as delivered by Matreya) in 5 mL of MeOH.

Subsequently the solution V1-A-534 was prepared as a mixture of 12 µL of Lyso-Gb1 stock solution and 5 mL DMSO/MeOH (1:1; v/v) as displayed in the following:

| Label of resulting solution | exp. conc. [µg/mL] | Volume of solution [µL] | solution | volume of solvent [mL] | solvent |
|---|---|---|---|---|---|
| V1-A-534 | 0.79968 | 12 | Lyso-Gb1-stock | 5 | DMSO/MeOH (1:1; v/v) |

Subsequently the Calibration Standards were prepared by spiking solution V1-A-534 or higher concentrated Calibration Standards into the solvent MeOH/water (1:1; v/v).

A detailed spiking scheme will be displayed in the following.

| Label of resulting solution | concentration [ng/mL] | Volume of solution [µL] | solution | volume of solvent [mL] | solvent | Volume [ml] |
|---|---|---|---|---|---|---|
| Std9A-534 | 102.12 | 366 | V1-A-534 | 2.5 | MeOH/water (1:1; v/v) | 2.866 |
| Std8A-534 | 40.970 | 162 | V1-A-534 | 3 | MeOH/water (1:1; v/v) | 3.162 |
| Std7A-534 | 15.321 | 353 | Std9A-534 | 2 | MeOH/water (1:1; v/v) | 2.353 |
| Std6A-534 | 6.1464 | 353 | Std8A-534 | 2 | MeOH/water (1:1; v/v) | 2.353 |
| Std5A-534 | 2.5906 | 135 | Std8A-534 | 2 | MeOH/water (1:1; v/v) | 2.135 |
| Std4A-534 | 1.0577 | 53 | Std8A-534 | 2 | MeOH/water (1:1; v/v) | 2.053 |
| Std3A-534 | 0.41004 | 55 | Std7A-534 | 2 | MeOH/water (1:1; v/v) | 2.055 |
| Std2A-534 | 0.15868 | 53 | Std6A-534 | 2 | MeOH/water (1:1; v/v) | 2.053 |
| Std1A-534 | 0.050049 | 39.4 | Std5A-534 | 2 | MeOH/water (1:1; v/v) | 2.0394 |

For calibration, calibration standards having seven concentration levels between 0.400 and 100 ng/mL were used, namely Calibration Standards Std3A-534, Std4A-534, Std5A-534, Std6A-534, Std7A-534, Std8A-534 and Std9A-534.

Preparation of Control Samples

Control samples were prepared by spiking solution V1-A-534 or a higher concentrated control sample into a blank matrix.

A detailed spiking scheme will be displayed in the following.

| Label of resulting solution | concentration [ng/mL] | Volume of solution [µL] | solution | volume of blank matrix [mL] | Volume [ml] |
|---|---|---|---|---|---|
| QC-A1-534 | 1.0013 | 173.6 | QC-C1-534 | 8.5 | 8.6736 |
| QC-B1-534 | 5.0008 | 944 | QC-C1-534 | 8.5 | 9.444 |
| QC-C1-534 | 50.029 | 634 | V1-A-534 | 9.5 | 10.134 |

Blank Matrix

As a blank matrix, human plasma of a healthy subject was used. A person skilled in the art will acknowledge that said plasma from a healthy subject will contain a native level of free lyso-Gb1. Said native level of free lyso-Gb1 is about 1.4 ng/ml according to the methods of the present invention. It is thus obvious that control samples prepared by spiking of the blank matrix, the blank matrix comprising said native level of free lyso-Gb1, also comprise said native level of free lyso-Gb1 in addition to the level of free lyso-Gb1 obtained by spiking with a concentrated solution or higher concentrated control sample. Accordingly, the level of free lyso-Gb1 in the control samples is as follows:

| QC-A1-534 | 1 ng/mL + native concentration in blank matrix |
| QC-B1-534 | 5 ng/mL + native concentration in blank matrix |
| QC-C1-534 | 50 ng/mL + native concentration in blank matrix |

A person skilled in the art will acknowledge that human plasma of a healthy subject used as blank matrix can be purchased at any commercial source known to the one skilled in the art. It is important to note that if accidentally plasma of a non-healthy subject, i.e. of a subject having Gaucher's disease, is used as the blank matrix, this will result in unusually high levels of free lyso-Gb1 in the control samples determined by the method according to the present invention and thus will be immediately recognized, as the tolerance of the method is determined as being within a range of 15% above or below the estimated levels of the controls subjected to the method according to the present invention.

Study Samples

Preparation of Internal Standard

The Internal Standard (IS1) stock solution was prepared dissolving 1.00 mg of Lyso-Gb2 (as delivered by Matreya) in 2 mL of DMSO/MeOH (1/1; vol/vol).

Subsequently the Internal Standard Working Solution was prepared as a mixture of 410 µL of IS1 stock solution and 500 mL of ethanol. The ethanol may be purchased from any commercial source, wherein the ethanol is absolute ethanol having a grade suitable for the methods described herein. A person skilled in the art will recognize that proteins contained in 50 µl of a sample have to precipitate if 100 µL of said Internal Standard working solution are added to the sample.

Storing of Samples and Solutions

Control samples or study samples either were immediately stored below −20° C. at once or aliquots were transferred into new glass vials before storing under the same conditions.

Concentrated solutions (stock solutions, V1-A-534 etc.) as well as Internal Standard stock solutions were frozen below −20° C. pending next spiking.

Internal Standard working solutions were stored between 2° C. and 8° C. until use. The present inventors have found that free lyso-Gb1 is stable in the above mentioned solutions. More precisely, the level of free lyso-Gb1 of a plasma and/or a serum sample of a Gaucher's disease patient determined by the methods according to the present invention were found to be identical, if the level of free lyso-Gb1 was determined in said samples prior to and after storage at 37° C. for 2 days. Accordingly, the solutions and samples of the present invention can be transported in a number of ways well known to one skilled in the art, wherein the use of a cold chain for transportation of patient material is preferred but not necessarily required. A person skilled in the art will also know methods and their respective conditions for appropriate storage of solutions and samples, wherein, for example, said solutions and samples may be stored for several weeks.

Sample Preparation for Analysis

All samples used in an analytical batch are prepared for analysis as follows:

Frozen samples were thawed at approximately 20 to 25° C. in a water bath taking from ambient conditions. After thawing the samples were mixed.

50 µL of the sample were transferred into a sample vial. 100 µL of Internal Standard working solution (in EtOH) was added to the sample.

The thus obtained mixture was subsequently mixed using a DVX-2500 Multi-tube vortex device at 2500 rpm for about 30 seconds.

The thus obtained mixture was centrifuged for phase separation at 4000 rpm for 2 minutes.

Transfer of a volume of the supernatant adequate to injection purposes (approx. 100 µL) into appropriate (conical) auto-sampler vials.

Methods

Chromatographic and Auto-Sampler Parameters

The samples prepared for analysis as described above were subsequently subjected to the method described in the following:

| Parameter | Scheduled range/description |
|---|---|
| Mobile phase solvent A | 50 mM FA in water |
| Mobile phase solvent B | 50 mM FA in ACN/acetone (1:1; vol/vol) |
| Chromatographic run | 0.0-4.0 min linear gradient: 5% B → 66% B |
| | 4.1-5.1 min isocratic: 100% B |
| | 5.1-5.9 min isocratic: 5% B |
| Flow | 0.9 mL/min |
| Injection volume | 5 µL |
| Injector flush | 0.1% TFA in 70% MeOH |
| Column + Precolumn | ACE 3 C8, 50 × 2.1 mm ID + Security Guard C8 |
| Column temperature | 60° C. |
| Retention time | approx. 3.4 to 3.6 min: lyso-Gb1 and lyso-Gb 2 (IS) |

The ACE 3 C8 column (ACE C8 column Nr. ACE-112-0502) used herein has been purchased from Advanced Chromatography Technologies, Aberdeen.

It will be appreciated by a person skilled in the art that parameters where a "+" range is indicated represent parameters which may be adjusted between sequences. A sequence as used herein, preferably is a batch of defined numbers of samples, preferably 250 in maximum analyzed sequentially, wherein parameters comprising flow and temperature remain unchanged. Adjustments and calibrations performed between sequences are known to those skilled in the art and comprise exchange of the column.

These adjustments within the specified limits are minor changes and are recorded within the raw data of the study at the measuring station.

Detection

The thus prepared samples were subsequently subjected to the detection method the parameters of which are described in the following:

| | |
|---|---|
| MS Ionisation mode: | Electrospray Ionisation (ESI) |
| MS polarity: | positive |
| MS detection mode: | Multiple reaction monitoring (MRM) |
| Vaporizer temperature: | 500° C. ± 50° C. |
| Ionisation voltage: | 5.5 kV |
| Collisionally activated dissociation (CAD) gas: | low |
| Gas 1: | Pressure = 45 psi |
| Gas 2: | Pressure = 60 psi |
| Curtain gas: | pressure = 40 psi |
| Lateral position: | 5 units |
| Vertical position: | 4 units |
| Quadrupole resolution | unit → unit |
| Transitions | 462.4 → 282.2 m/z lyso-Gb1 |
| | 624.5 → 282.2 m/z lyso-Gb2 |
| | (Internal Standard) |
| DP (declustering potential) | 40 V |
| CXP (collision cell exit potential) | 8 V |

A person skilled in the art will acknowledge that methods for detecting free lyso-Gb1 and/or determining the level of free lyso-Gb1 in a sample from a subject using mass spectrometric analysis may also employ other transitions and fragments which allow for specific detection of and/or quantification of free lyso-Gb1 in said sample from a subject.

Evaluation and Calculation of Results

To evaluate and to calculate results obtained with the above specified methods the following protocol were applied.

Rounding Procedure

Concentration data fed into and retrieved from the chromatographic data system (CDS) were rounded to five significant digits. Further calculations in the spreadsheet were performed to full computational accuracy and subsequently rounded to the significant digits/decimal places to be reported. Hence, deviations of intermediate results might occur caused by rounding. Accuracy and coefficients of variation (CV) will be reported with one and two decimal places, respectively.

Note referring to the rounding procedure: The last digit reported would be up-rounded if the subsequent digit was equal or greater than "5".

Regression and Statistics

Based on Calibration Standards the calibration curve fitting were established using the data processing software by means of peak area ratios (peak area of free lyso-substance contained in the sample from the subject/peak area of Internal Standard). Free lyso-substance concentrations were evaluated using an Internal Standard methodA quadratic ($y=ax^2+bx+c$) regression model using the weighting factor 1/conc. will be used to calculate the concentration of each analyte in every batch to be evaluated. The concentrations were calculated by means of the following formula:

$$\text{concentration} = \frac{-b \pm \sqrt{b^2 - 4a(c - \text{peak area ratio})}}{2a}$$

Based thereon mean values, precision results (in terms of CVs) and accuracies (formula shown below) will be calculated using the program "Lotus 123".

$$\text{accuracy (\%)} = \frac{\text{calculated concentration}}{\text{expected concentration}} \cdot 100$$

Appropriate statistical models are described in e.g.

Green, J. R., Statistical Treatment of Experimental Data (Elsevier, New York, 1977), page 210 ff.

Lothar Sachs, Angewandte Statistik—Anwendung statistischer Methoden (Springer, Berlin, Heidelberg, N.Y., Tokyo 1984)

Software

Data acquisition, data processing, statistics and calculations were performed using Analyst® software 1.4.2 or higher (AB SCIEX, USA/Canada) as well as Lotus 1-2-3 97 or higher (Lotus Corp, USA).

Handbooks

| | |
|---|---|
| Handbook | Arbeiten mit SmartSuite 97 (Lotus Development Corp., 1997) |
| Documentation of software used | Documentation of Analyst ® Software (AB SCIEX, USA/Canada): |
| | Operator's Manual & Operator's Manual Addendum "New Functionality in Analyst 1.2" and Online Help System Analyst 1.4 (or higher) |

Example 2: Genetic Testing and Classification of Study Participants

After consenting of patients to participation in the study, patients were subjected to a genetic testing for mutations of the glucocerebrosidase gene. Accordingly, 5 to 10 ml of EDTA blood were sequenced according to Seeman et al. (Seeman et al., 1995). Were appropriate other genes beside the glucocerebrosidase gene were sequenced in addition, particularly in controls. Furthermore the chitotriosidase gene was sequenced for detection of the 24 bp duplication as mentioned above. Said genetic testing was controlled using test samples of age and sex matched control patients. 253 subjects were tested.

According to the result of the above described genetic testing, patients participating in the study were classified into the following groups:

1.) Patients having Gaucher's disease: gold standard for the diagnosis was the detection of two pathogenic mutations within the glucocerebrosidase gene, either homozygous or compound heterozygous (group is named in the figures as "Gaucher");

2.) Patients being heterozygous carriers of one mutation within the glucocerebrosidase gene (typically relatives of affected patients) (group is named in the figures as "heterozygote")

3.) patients with other lysosomal storage disorders as control (group is named in the figures as "other LSD"); this comprises patients with sphingomyelinase deficiency (Niemann Pick A/B), Krabbe disease and Niemann Pick C1; all diagnoses have been proven by the detection of two pathogenic mutations 4.) healthy age and gender matched controls (group is named in the figures as "control") The following table 1a shows the classifying of patients into the above described groups according to the results of the above described genetic testing.

TABLE 1a

Subjects classified by results of genetic analysis

| | cases | | | | | |
|---|---|---|---|---|---|---|
| | valid | | missing | | total | |
| Groups (Dgn) | N | percentage | N | percentage | N | percentage |
| control | 140 | 100.0% | 0 | 0% | 140 | 100.0% |
| Heterozygous (carrier) | 13 | 100.0% | 0 | 0% | 13 | 100.0% |
| Gaucher | 59 | 100.0% | 0 | 0% | 59 | 100.0% |
| other LSD | 20 | 100.0% | 0 | 0% | 20 | 100.0% |

The distribution of the gender of the 232 German patients as well as the distribution of the gender of 21 Israeli patients are depicted in Table 1 b.

TABLE 1b

232 German subjects and 21 Israeli classified by gender

| | Germans | | Israel | |
|---|---|---|---|---|
| | N | % | N | % |
| total | 232 | | 21 | |
| Sex | | | | |
| male | 146 | 57.0 | 11 | 52.4 |
| female | 110 | 43.0 | 10 | 47.6 |

The following table 1c shows the distribution of the age of the 232 German patients and the classification of said patients based on the results of the above described genetic testing as well as the gender of said patients.

Figure 1B:
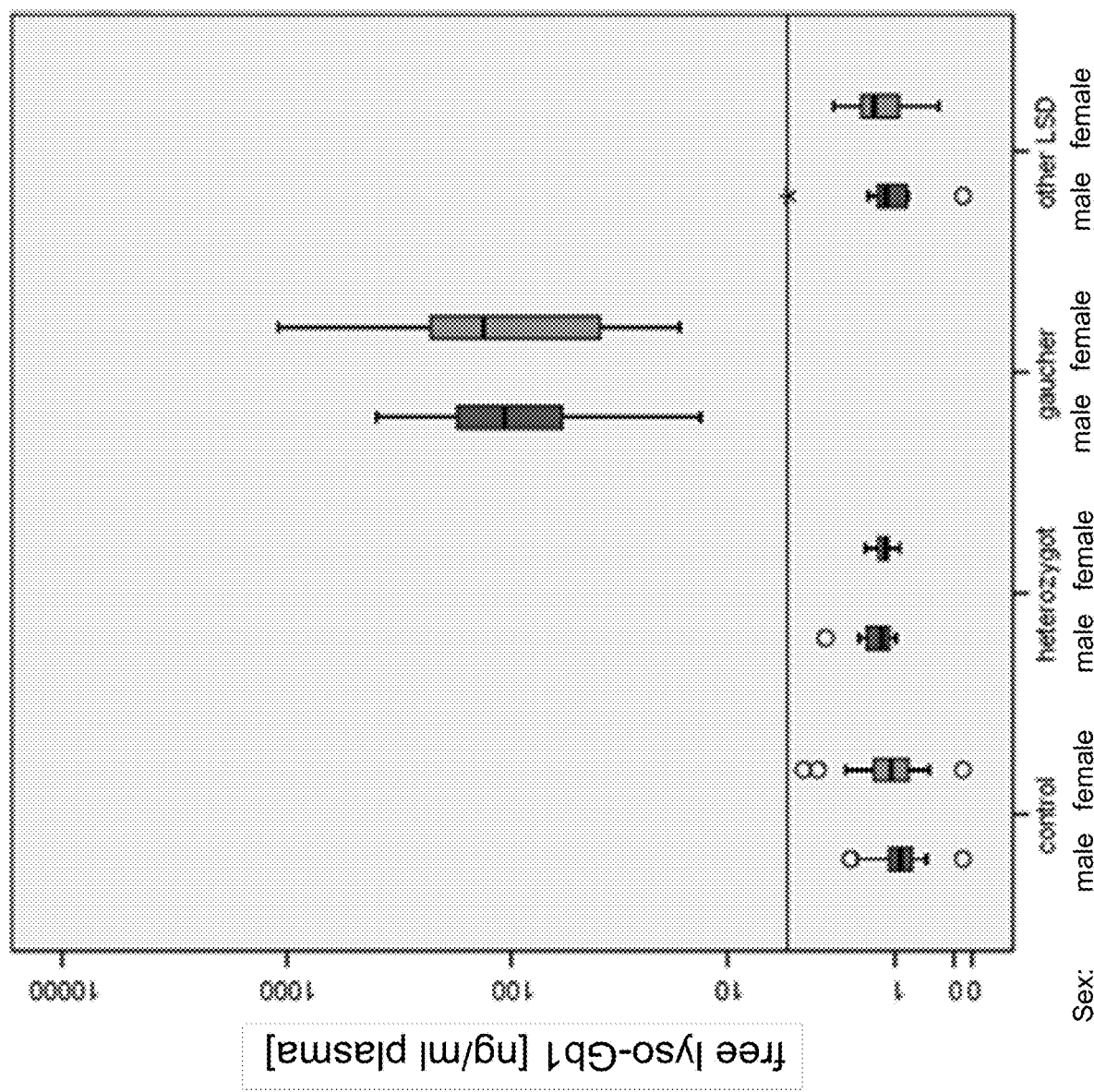
FIG. 1B is a boxplot indicating the levels of free lyso-Gb1 as depicted in FIG. 1A additionally grouped by gender of the subjects; the y-axis represents the logarithmised levels of free lyso-Gb1 in ng/ml determined in plasma of patients by the method according to the present invention, wherein the x-axis represents groups of patients, which have been grouped as described in Example 2 and additionally by the gender of the patients. The boxplot represents the $25^{th}$ and $75^{th}$ percentile of each group of patients by the bottom and top of the box, respectively; the band near the middle of the box represents the $50^{th}$ percentile (e.g. the median) of each group; The whiskers represent one standard deviation above and below the mean of the data; Any data not included between the whiskers is shown as an outlier with a small circle or star. The horizontal line represents the cut-off level of 5 ng/ml.

The level of free lyso-Gb1 in samples of said 253 subjects was determined according to the method described in Example 1. The level of free lyso-Gb1 in samples from said patients depending on the classification by genetic analysis is shown in FIG. 1A. FIG. 1B shows the level of free lyso-Gb1 in samples from said patients depending on the classification based on the genetic analyses and on the gender of the patients.

The type of mutation and the distribution of the types of mutations of the glucocerebrosidase gene in patients classified as Gaucher's disease patients according to the results obtained in the genetic testing as described above are depicted in Table 2 below.

TABLE 2

Distribution of mutations being detected in the German Gaucher population (166 alleles)

| type of mutation | n | % |
|---|---|---|
| N370S | 54 | 32.5% |
| L444P | 33 | 19.9% |
| RecNciI | 15 | 9.0% |
| G202R | 4 | 2.4% |
| D409H | 3 | 1.8% |
| Rec | 3 | 1.8% |
| G355A | 2 | 1.2% |
| IVS2+1A>G | 2 | 1.2% |
| L335V | 2 | 1.2% |
| L444R | 2 | 1.2% |
| R120W | 2 | 1.2% |
| R285H | 2 | 1.2% |
| RecAP2 | 2 | 1.2% |
| T226I | 2 | 1.2% |
| T231R | 2 | 1.2% |
| T491I | 2 | 1.2% |
| V398L | 2 | 1.2% |
| A46term | 1 | 0.6% |
| A495P | 1 | 0.6% |
| A88P | 1 | 0.6% |
| C287F | 1 | 0.6% |
| F216Y | 1 | 0.6% |
| G82A | 1 | 0.6% |
| H255Q | 1 | 0.6% |
| I93F | 1 | 0.6% |
| IVS3+1G>A | 1 | 0.6% |
| L324Q | 1 | 0.6% |
| N234S | 1 | 0.6% |
| N409S | 1 | 0.6% |
| P161R | 1 | 0.6% |
| P178S | 1 | 0.6% |

TABLE 1c

Patient characteristics of 253 subjects

| | Healthy controls | Heterozygous carrier | Gaucher | Other LSD |
|---|---|---|---|---|
| N subjects | 140 | 13 | 80 | 20 |
| N samples | 155 | 15 | 287 | 28 |
| Age in years (median, interquartile range) (number of cases) | 28.5 (4.8-47.3) (n = 134) | 35.0 (30.5-58.5) (n = 13) | 30.0 (8.0-48.0) (n = 79) | 23.5 (4.0-43.5) (n = 14) |

| | male | female | male | female | male | female | male | female |
|---|---|---|---|---|---|---|---|---|
| n | 79 | 61 | 8 | 5 | 45 | 35 | 12 | 8 |
| Age (median, interquartile range) | 25.5 (5.3-47.0) | 34.0 (3.8-48.8) | 33.5 (26.0-51.8) | 39.0 (33.0-69.5) | 22.0 (7.5-50.0) | 32.5 (12.8-43.3) | 21.0 (3.3-30.3) | 34 (8.8-45.8) |

TABLE 2-continued

Distribution of mutations being detected in
the German Gaucher population (166 alleles)

| type of mutation | n | % |
|---|---|---|
| P29X | 1 | 0.6% |
| P68fs | 1 | 0.6% |
| Q326K | 1 | 0.6% |
| R120Q | 1 | 0.6% |
| R257ter | 1 | 0.6% |
| R359Q | 1 | 0.6% |
| R502C | 1 | 0.6% |
| R502H | 1 | 0.6% |
| RecAF3 | 1 | 0.6% |
| RecAF4 | 1 | 0.6% |
| RecAH3 | 1 | 0.6% |
| RecTL | 1 | 0.6% |
| S13L | 1 | 0.6% |
| S146L | 1 | 0.6% |
| S237F | 1 | 0.6% |
| S364N | 1 | 0.6% |
| V398L | 1 | 0.6% |
| W184R | 1 | 0.6% |

Measurement of Chitotriosidase Activity

Chitotriosidase activity was measured as essentially described in Hollak et al. (Hollak C E, van Weely S, van Oers M H, Aerts J M. Marked elevation of plasma chitotriosidase activity. A novel hallmark of Gaucher disease. J Clin Invest. 1994 March; 93(3):1288-92) by incubating 10 µl of EDTA plasma or serum with 100 µl of 0.022 mM fluorogenic substrate 4-methylumbelliferyl-fl-D-NN,N'-triacetylchitotriose (4 MU-chitotrioside; Sigma Aldrich, ST. Louis, Mo., USA) as substrate in McIlvain buffer (0.1 M citric acid/0.2 M sodium phosphate, pH 5.2) at 37° C. In Gaucher's disease patients, samples were diluted 50× in demineralized water before incubation. After 30 min the reaction was stopped with 200 µl of 0.5 M glycine/NaOH buffer (pH 10.5) by mixing at room temperature. The substrate hydrolysis by chitotriosidase produces the fluorescent molecule 4-methylumbelliferone, which was quantified with a fluorimeter (Tecan Group Ltd., Männedorf, Switzerland), excitation at 366 nm and emission at 446 nm, and compared with a standard 4-methylumbelliferone calibration curve. Chitotriosidase activity was expressed as nanomoles of substrate hydrolyzed per hour per milliliter of incubated serum.

Quantification of CCL18

CCL18 in plasma was quantified with a DuoSet ELISA Development kit purchased from R&D Systems, Minneapolis, Minn., USA in accordance with the manufacturer's instructions. The sensitivity of the method was 5 pg/ml.

Example 3: Diagnosis of Gaucher's Disease Using Free Lyso-Gb1 as a Biomarker

Figure 5A:
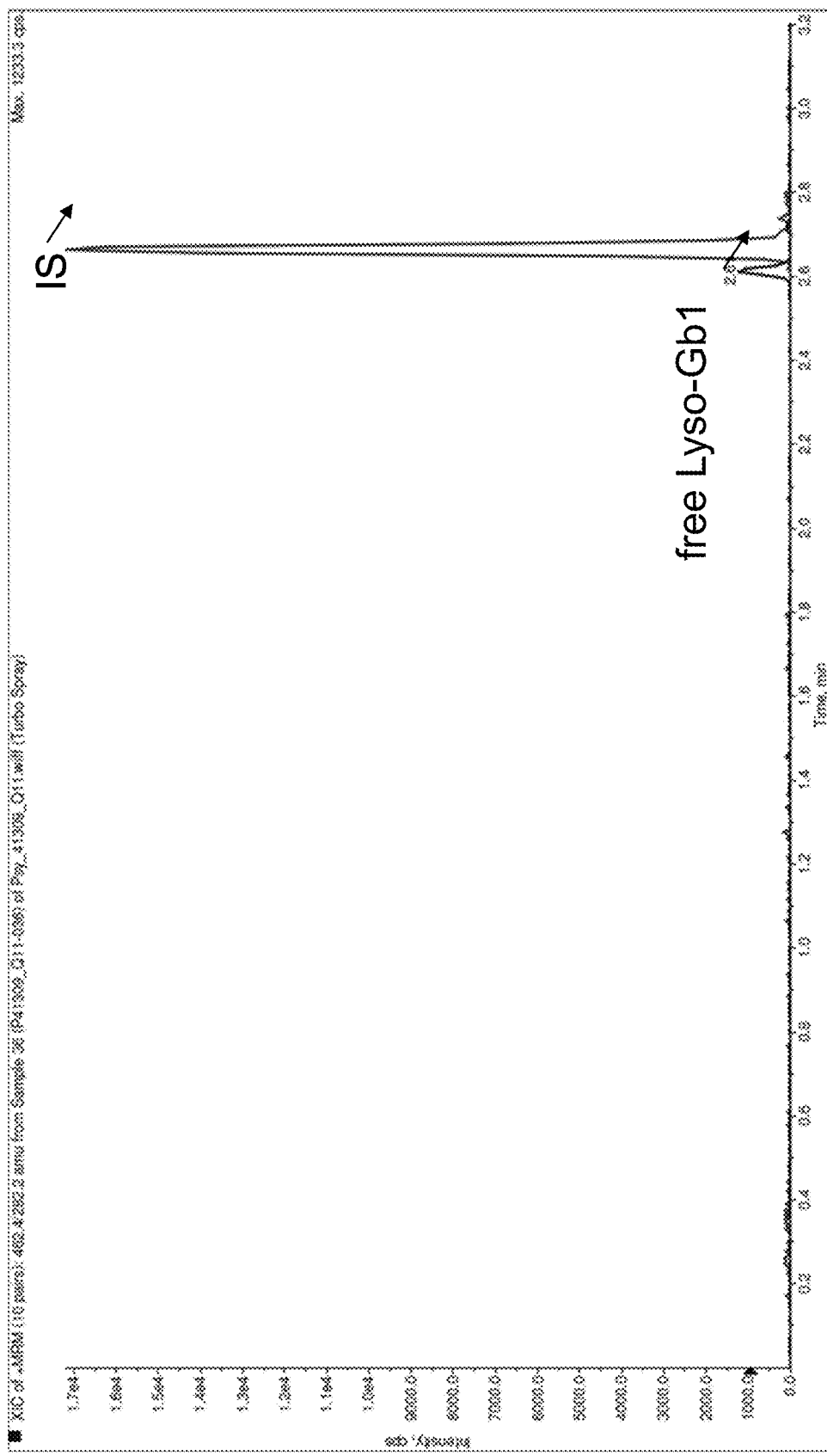
FIG. 5A is an HPLC-mass spectrometry chromatogram displaying peak intensity in cps of free lyso-Gb1 and IS of a sample from a healthy subject as a function over the retention time in minutes. The retention time of a substance as used herein, preferably is depicted on the x-axis and is the elapsed time between the time of injection of a solute, e.g. a biomarker according to the present invention and/or an internal standard, and the time of elution of the peak maximum of said solute. A person skilled in the art will acknowledge that the retention time of a substance according to the herein described methods is a unique characteristic of said solute and can be used for identification purposes. Internal Standard working solution comprising Lyso-Gb2 as an internal standard was added to the sample as described in Example 1. It is important to understand that by said addition of IS to the sample, i.e. spiking of the sample, to be subjected to the method according to the present invention, the concentration of IS in the sample is known and by determining the area under the peak, i.e. the peak area, of the internal standard in said HPLC-mass spectrometric chromatogram the relation between a peak area and a concentration of a substance, e.g. of IS and/or a biomarker thus can be calculated. More precisely, a person skilled in the art will acknowledge that a peak area of a substance depicted in an HPLC-mass spectrometric chromatogram, such as the HPLC-mass spectrometric chromatogram depicted in FIG. 5A, FIG. 5B or FIG. 5C, represents a measure for an amount of said substance subjected to an HPLC-mass spectrometric analysis. Moreover, a person skilled in the art will be able to calculate the amount of the substance in a sample from a subject subjected to an HPLC-mass spectrometric analysis, e.g. the amount of free lyso-Gb1 in a sample subjected to the method of the present invention, using a ratio of the peak area of free lyso-Gb1, the amount of which is to be determined by said method and the peak area of IS, e.g. free lyso-Gb2; as well as calibration curves generated with said method and said free lyso-Gb1 and/or IS. Accordingly, this allows subsequently for determining a level of free lyso-Gb1.
Figure 5B:
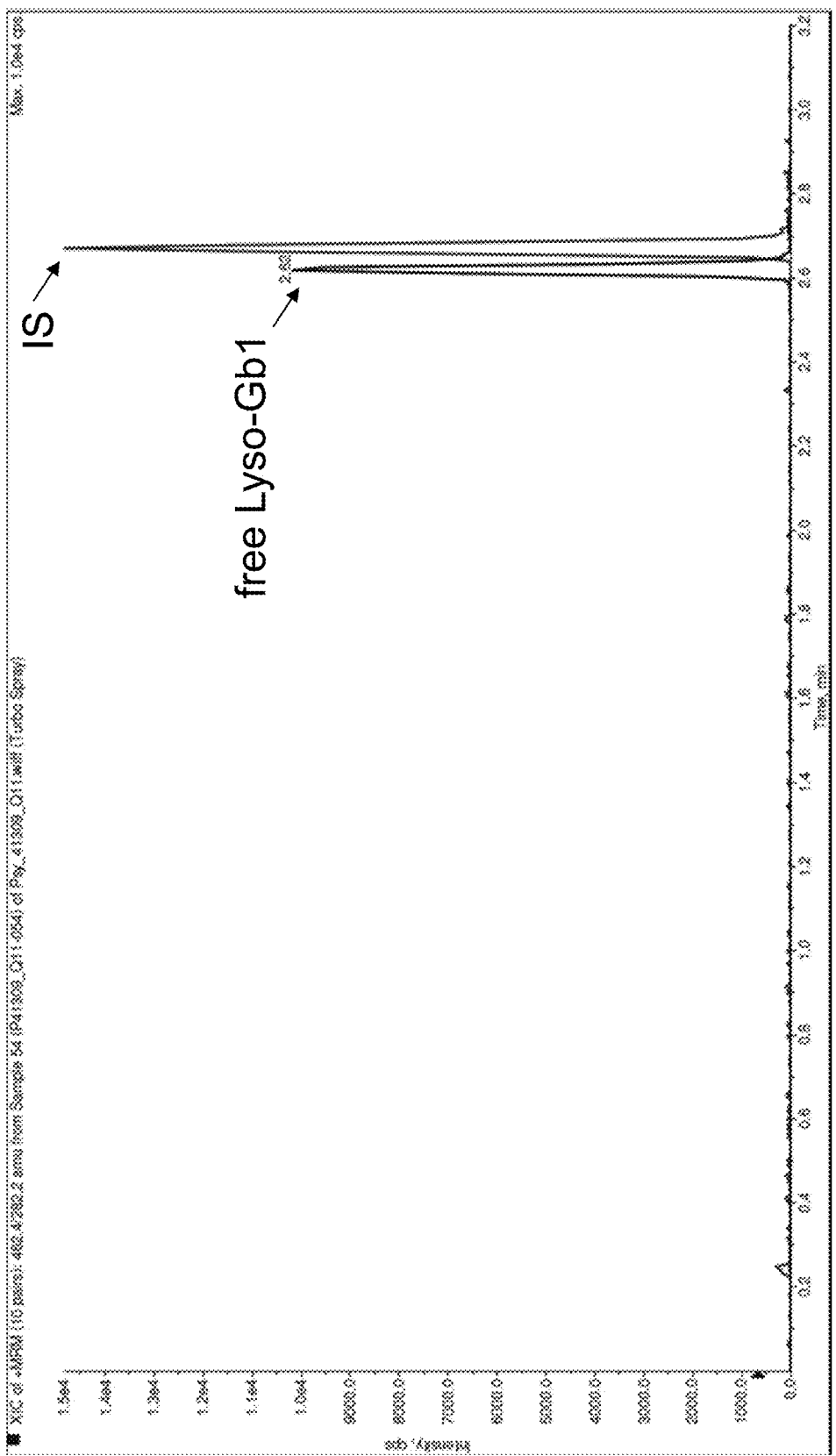
FIG. 5B is an HPLC-mass spectrometry chromatogram displaying peak intensity of free lyso-Gb1 and IS of a sample from a Gaucher's disease patient, wherein a level of 17.1 ng/ml free lyso-Gb1 was determined according to the method of the present invention as essentially described in Example 1. Comparing said level of the biomarker in the sample from the subject to a cut-off level of 5 ng/ml, which has been selected such that a sensitivity for diagnosing Gaucher's disease in a subject according to the methods of the present invention is 100% and that a specificity for diagnosing Gaucher's disease in a subject according to the methods of the present invention is 100%, an elevated level of the biomarker in the sample from the subject compared to the cut-off level is indicative for the subject for suffering from Gaucher's disease.
Figure 5C:
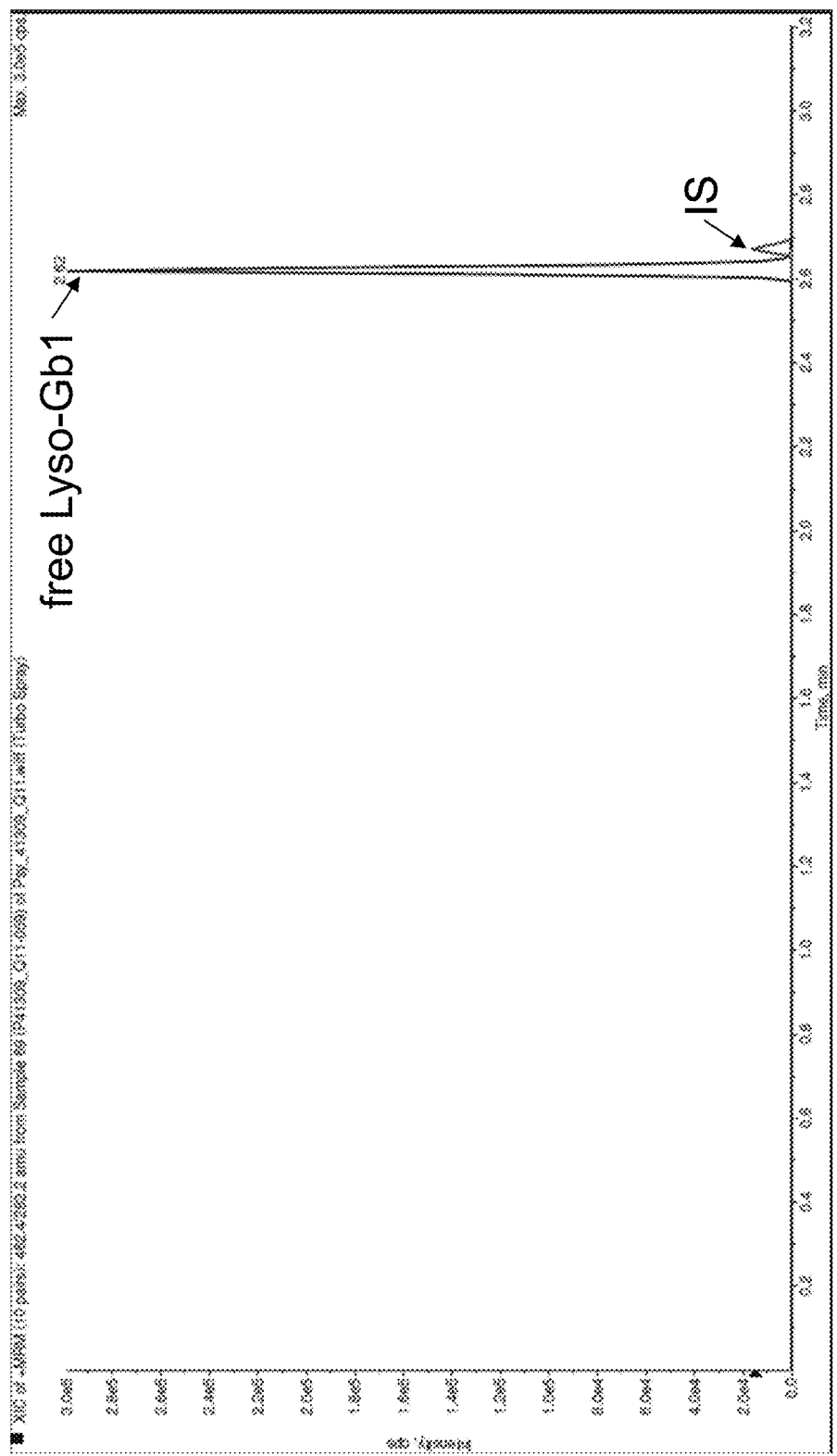
FIG. 5C is an HPLC-mass spectrometry chromatogram displaying peak intensity of free lyso-Gb1 and IS of a sample from a Gaucher's disease patient, wherein a level of 319 ng/ml free lyso-Gb1 was determined according to the method of the present invention as essentially described in Example 1. Comparing said level of the biomarker in the sample from the subject to a cut-off level of 5 ng/ml, which has been selected such that a sensitivity for diagnosing Gaucher's disease in a subject according to the methods of the present invention is 100% and that a specificity for diagnosing Gaucher's disease in a subject according to the methods of the present invention is 100%, an elevated level of the biomarker in the sample from the subject compared to the cut-off level is indicative that the subject is suffering from Gaucher's disease.

The protocols described in Example 1 above were used to generate HPLC-mass spectrometric chromatograms of 485 blood samples derived from the 253 subjects. Exemplary HPLC-mass spectrometric chromatograms displaying peak intensity of free lyso-Gb1 and IS of three samples from two Gaucher's disease patients and one healthy control person are depicted in FIG. 5A, FIG. 5B and FIG. 5C.

Gold standard for the classification of patients into the group "Gaucher", was based on the sequencing of the entire coding area as well as the intron-exon-boundaries of the glucocerebrosidase gene according to the genetic testing as described in Example 2 resulting in the detection of either a homozygous mutation or a compound heterozygosity.

The results of a determination of the levels of Chitotriosidase or CCL18 in samples from patients were available in 58 or 44 Gaucher's disease patients, respectively. Said results were obtained as described in Example 2.

For comparing the diagnostic value of the different biomarkers and for the calculation of correlations between the biomarkers the data obtained by the method described above was first aggregated by using the earliest measured level of every marker for Gaucher's disease patients before therapy and the highest level for non-Gauchers for a particular patient if more than one blood sample was available.

Paired sample statistical techniques were used for the comparison of two biomarkers. The method exploits the mathematical equivalence of the AUC to the Mann-Whitney U-statistic (Delong E. R., Delong D. M., Clarke-Pearson D. L. (1988) Comparing the areas under two or more correlated receiver operating characteristic curves: a nonparametric approach, Biometrics, 44, 837-45.).

The accuracy of levels of the different biomarkers (free lyso-Gb1, Chitotriosidase and CCL18) obtained by the method described in Example 1 above was evaluated to discriminate patients with Gaucher's disease from patients without having Gaucher's disease using Receiver Operating Characteristic (ROC) curve analysis (Metz C.E. (1978) Basic principles of ROC analysis, Semin Nucl Med, 8, 283-98; Zweig M. H., Campbell G. (1993) Receiver-operating characteristic (ROC) plots: a fundamental evaluation tool in clinical medicine, Clin Chem, 39, 561-77). Measurement of Chitotriosidase activity and CCL18 was performed as described in Example 2 herein.

The ROC curves were calculated using PASW Statistics 18, Release Version 18.0.2 (©SPSS, Inc., 2009, Chicago, Ill., www.spss.com). The comparisons of ROC curves and the linear mixed models were done using SAS software, Version 9.2 of the SAS System for Windows. (©, 2008 SAS Institute Inc., Cary, N.C., USA).

Figure 2A:
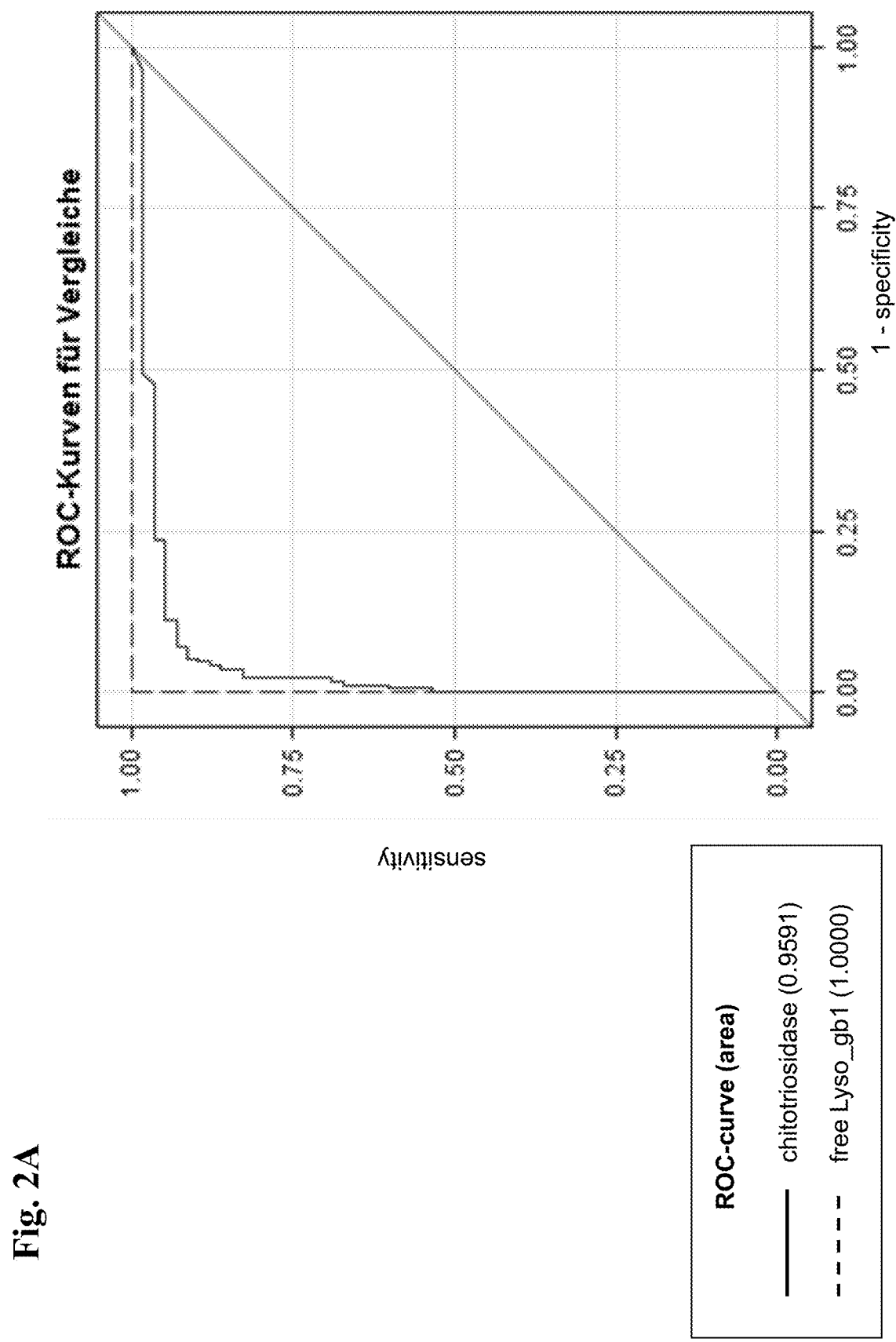
FIG. 2A is a graph showing receiver operating characteristics (ROC) curves of free lyso-Gb1 and chitotriosidase; the x-axis represents "1-specificity" and the y-axis represents the sensitivity. Free lyso-Gb1 demonstrates a 100% sensitivity and 100% specificity, wherein chitotriosidase has at the best a sensitivity of 0.9591 or 95.91%, respectively.
Figure 2B:
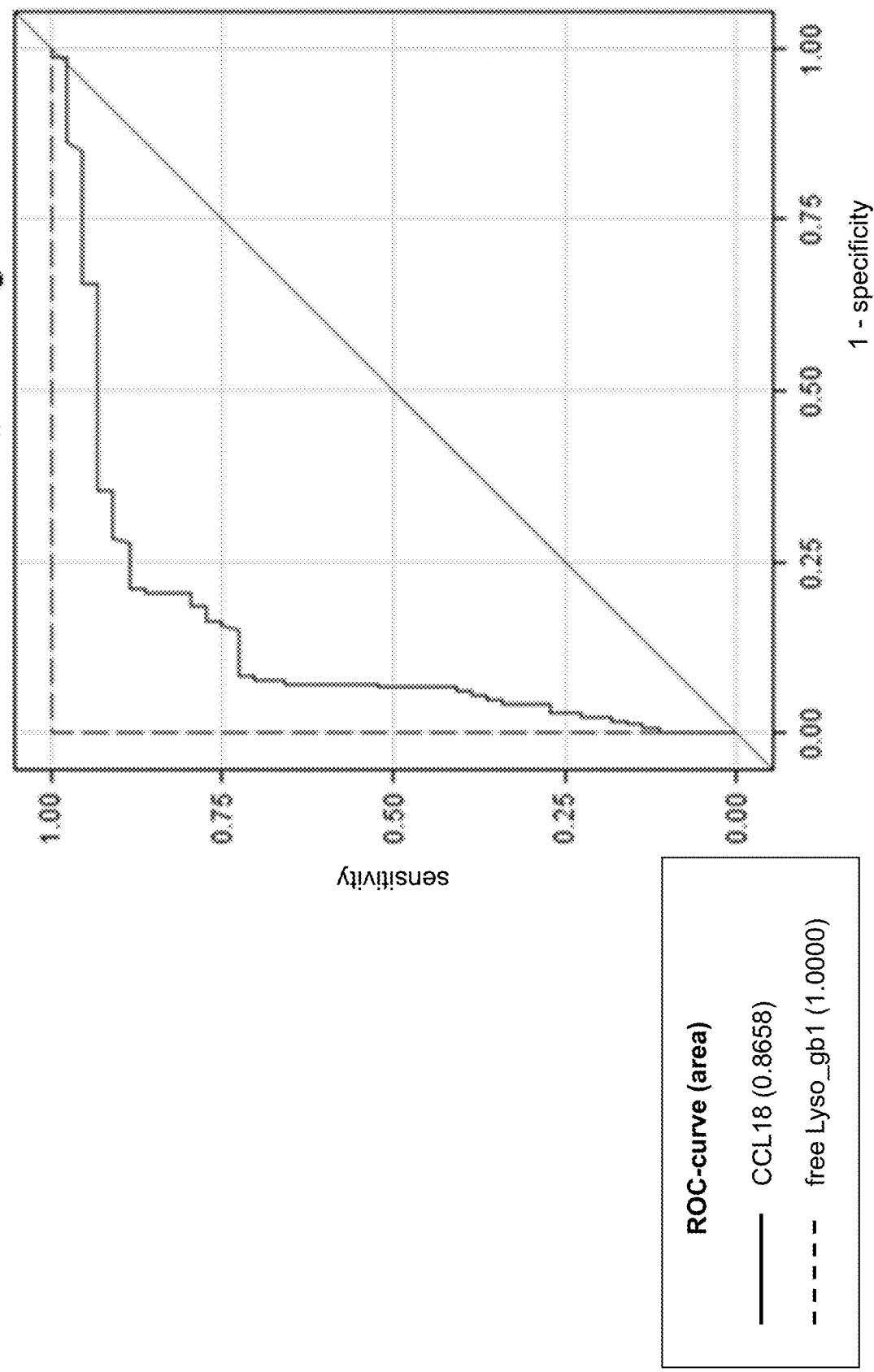
FIG. 2B is a graph showing receiver operating characteristics (ROC) curves of free lyso-Gb1 and CCL18; the x-axis represents "1-specificity" and the y-axis represents the sensitivity. Free lyso-Gb1 demonstrates a sensitivity of 100% and a specificity of 100%, wherein CCL18 has at the best a sensitivity of 0.8658 and 86.58%, respectively.

The ROC-curves comparing accuracy of levels of chitotriosidase and free lyso-Gb1 are shown in FIG. 2A and the ROC-curves comparing accuracy of levels of CCL18 and free lyso-Gb1 are shown in FIG. 2B, respectively.

The results depicted in the ROC-curves shown in FIG. 2A and FIG. 2B also show the specificity and the sensitivity of the method according to the present invention depending on different cut-off levels of free lyso-Gb1. Table 3 below shows accordingly the Sensitivity and the Specificity of the method according to the present invention depending on different cut-off levels of free lyso-Gb1.

TABLE 3

Sensitivity and Specificity of the method for diagnosing Gaucher's disease depending on the cut-off level of free lyso-Gb1 in the German subjects (n = 232)

| Cut-off level | >2.8 [ng/mL] | >4.1 [ng/mL] | >5 [ng/mL] |
|---|---|---|---|
| Sensitivity | 100.0% | 100.0% | 100.0% |
| Specificity | 97.7% | 99.4% | 100.0% |

Comparing the level of the biomarker in a sample from a subject determined by the method according to the present invention to a cut-off level, preferably a cut-off level allowing for a diagnosis having high specificity and high sensitivity thus allows for diagnosing Gaucher's disease in said subject, wherein an elevated level of the biomarker in the sample from the subject compared to the cut-off level is indicative for the subject for suffering from or for being at risk for developing Gaucher's disease and wherein a lower level of the biomarker in the sample from the subject compared to the cut-off level is indicative for the subject for not suffering from or for not being at risk for developing Gaucher's disease.

The area under the curve (AUC) and the 95% confidence limits for the different biomarkers are reported in table 4.

TABLE 4

Sensitivity and specificity for different biomarkers with regard to diagnose Gaucher.

| Cut-off level | Chitotriosidase (n = 228/58 Gaucher) >145 [nmolMU/h/ml] | CCL18 (n = 210/44 Gaucher) >166 [ng/ml] | free lyso-Gb1 (n = 232/59 Gaucher) >5 [ng/mL] |
|---|---|---|---|
| Sensitivity | 93.1% | 79.5% | 100.0% |
| Specificity | 90.0% | 79.5% | 100.0% |
| AUC and 95% CI in ROC Analysis | 0.96 (0.92-1.00) | 0.87 (0.80-0.93) | 1.00 (1.00-1.00) |

Accordingly, in table 3 the sensitivity and the specificity of the depicted biomarkers used in a method for diagnosing Gaucher's disease in a sample from a subject is compared using a cut-off level having the highest AUC in the respective method using the respective biomarker. Depicted is the ideal cut-off level of the respective method. Measurement of Chitotriosidase activity and CCL18 was performed as described in Example 2 herein. Free lyso-Gb1 was determined according to the method of the present invention. The ideal cut-off level is 5 ng/ml.

A person skilled in the art will acknowledge that the method according to the present invention using free lyso-Gb1 as a biomarker for diagnosing Gaucher's disease is clearly advantageous over methods using CCL18 or Chitotriosidase. This is especially true since at least 6% of the Caucasian population and up to 35% e.g. of the Latin American population, including those with Gaucher's disease, are deficient in chitotriosidase activity.

Accordingly, levels of free lyso-Gb1 determined in a sample from a subject according to the method of the instant application higher than 5.0 ng/mL allow for diagnosing that the subject is suffering from or is at risk for developing Gaucher's disease with a sensitivity of and with a specificity of 100%.

Example 4: Analysis of Change of Biomarkers Over Time

The method and patients used in connection with this Example were those as described in Examples 1 to 3.

For analyzing how the level of biomarkers changed over time in patients having Gaucher's disease non aggregated data was analyzed for those patients for whom more than one blood sample was analyzed. A time point zero was set to the first measure under therapy for every patient.

Figure 3A:
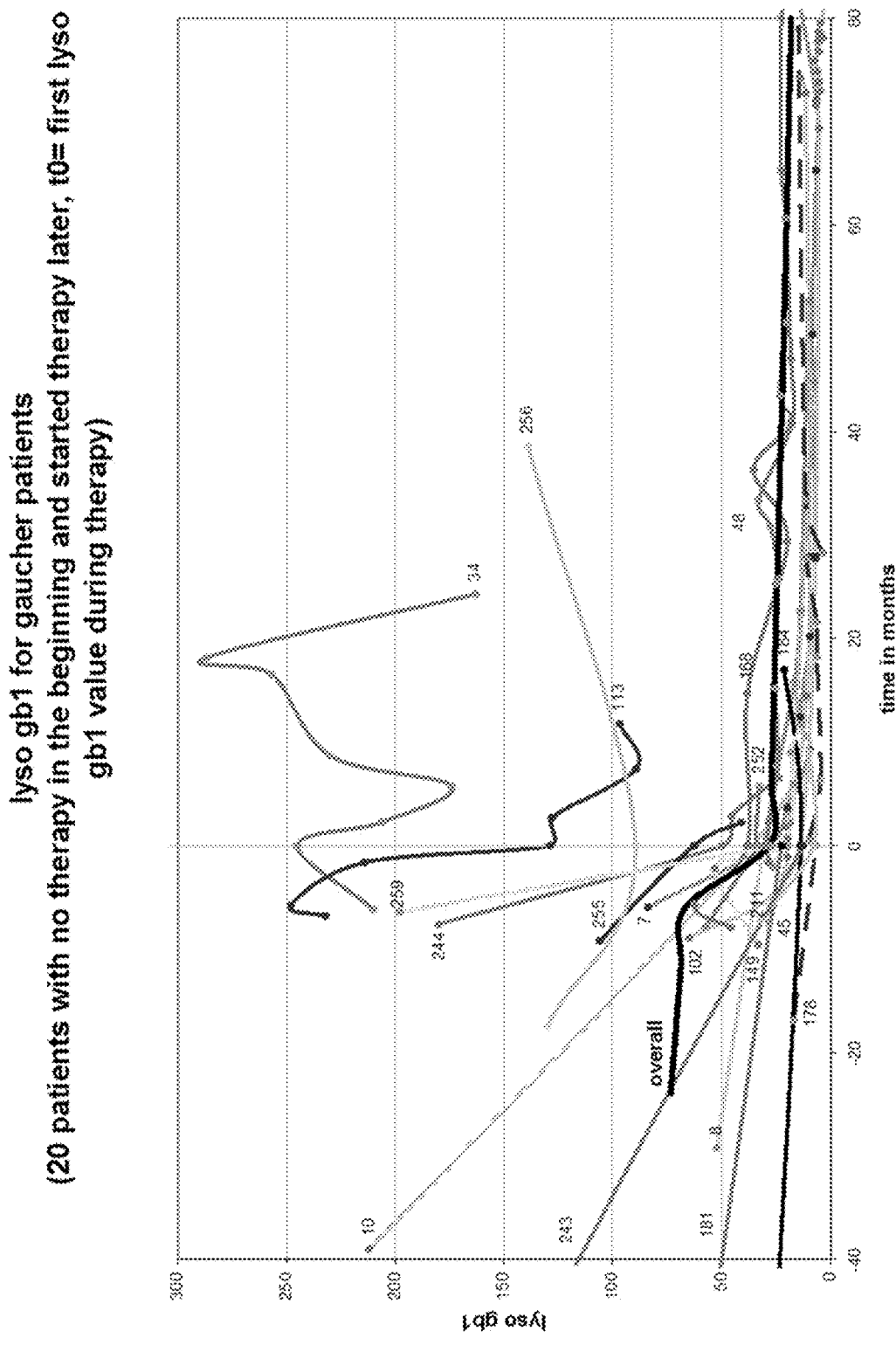
FIG. 3A The y-axis represents levels of free lyso-Gb1 as a function over time determined by the method according to the present invention in ng/ml of plasma of 20 German Gaucher's disease patients which were subjected to therapy, more precisely ERT, during the course of the study. Each curve and each patient number, respectively, represents levels determined in plasma collected from the same patient at different time points as indicated on the x-axis. The x-axis represents the time points of plasma collection, wherein time point zero indicates the first measure under therapy for each patient. For the analysis of the change of the level of free lyso-Gb1 over time in Gaucher's disease patients as described in Example 3 non aggregated data was used for those patients for which more than one blood sample has been analysed.
Figure 3C:
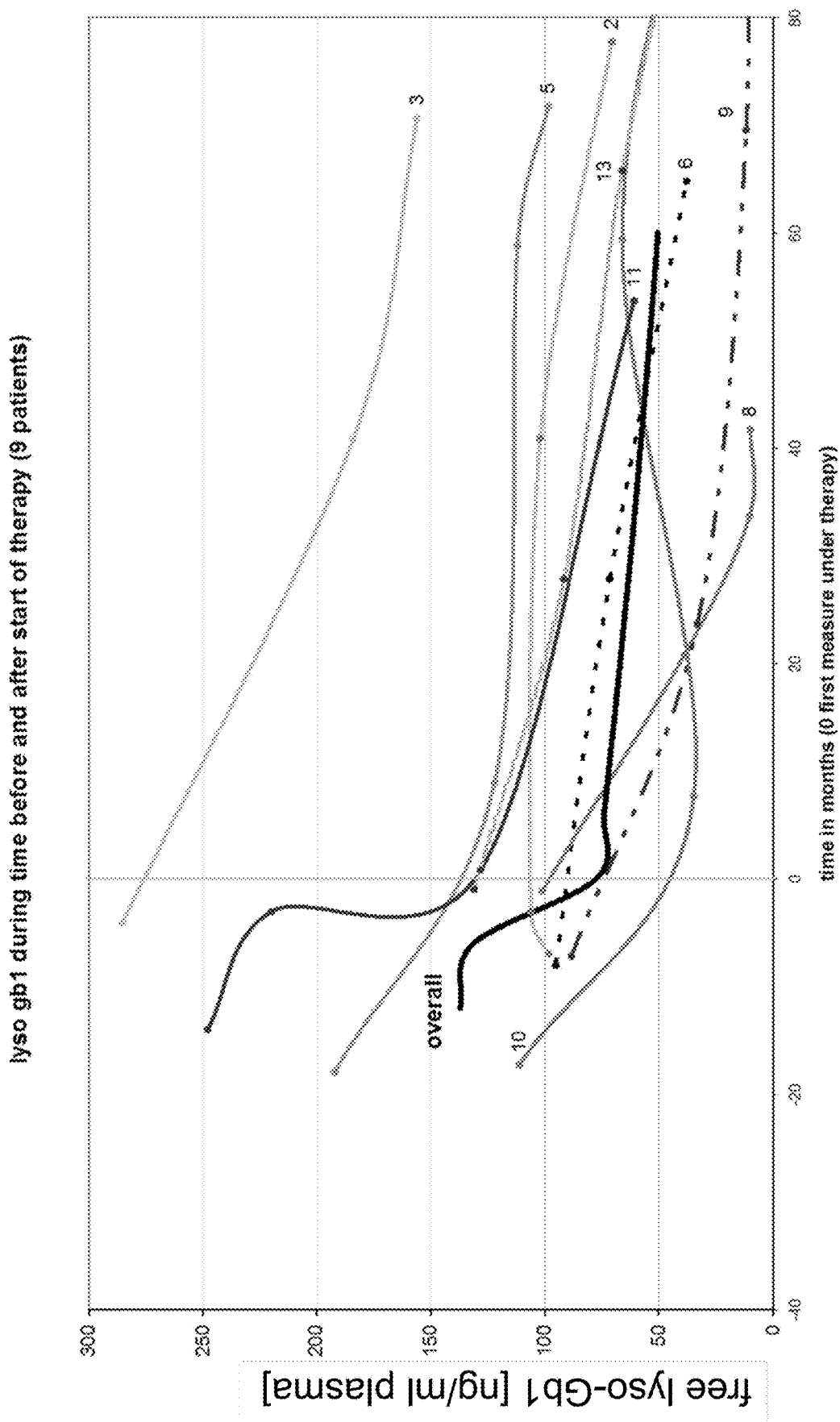
FIG. 3C is a diagram showing free lyso-Gb1 as a function over time with the free lyso-Gb1 being determined by the method according to the present invention in ng/ml of plasma of a total of 9 Israeli Gaucher's disease patients during time before and after the start of the therapy. The x-axis indicates the time in month, wherein "0" indicates the first point in time after start of therapy. The curve labeled with "overall" depicts the regression based values of free lyso-Gb1.
Figure 3D:
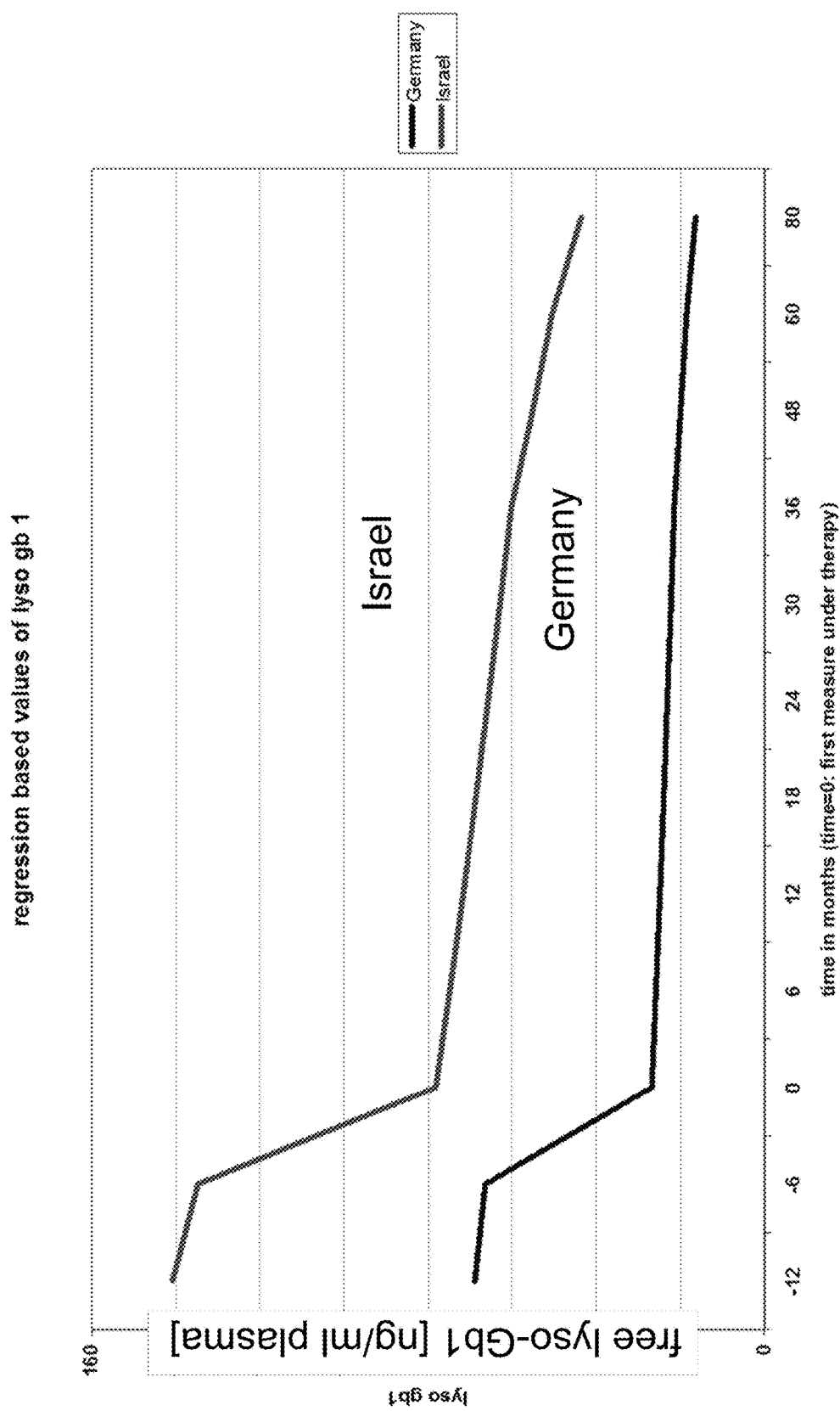
FIG. 3D is a diagram showing the regression based values of free lyso-Gb1 as a function over time determined by the method according to the present invention in ng/ml of plasma of a Israeli and German Gaucher's disease patients during time before and after the start of the therapy. The x-axis indicates the time in months, wherein "0" indicates the first point in time after start of therapy. The curve labeled with "overall" depicts the regression based values of free lyso-Gb1.

The levels of free lyso-Gb1 over time for individual patients are shown in FIG. 3A, FIGS. 3B and 3C.

To test for the significance of a time dependent reduction of free lyso-Gb1 levels indicative for a successful therapy, free lyso-Gb1 levels after start of a therapy were compared to free lyso-Gb1 levels before start of a therapy using linear mixed models. Untreated patients demonstrate no significant reduction of free lyso-Gb1 over the time.

Therefore the values of free lyso-Gb1 levels were logarithmised to overcome the skewness in the distribution of the values. To account for the heterogeneity between patients in the starting values as well as in the rate of change random intercept and slope models were used. In all models the observed heterogeneity was statistically significant. Only p-values for the linear time reduction are reported.

The values for time and those values which incorporated a squared term for time were centered to test for a curvilinear relation between time and marker level for Chitotriosidase and for CCL18. For free lyso-Gb1 the squared term did not improve the model and was not incorporated in the final model.

As a therapy German patients have been treated with 40 U/kg body weight in the mean, wherein units refers to units of recombinant glucocerebrosidase in ERT. The reduction in free lyso-Gb1 is specifically intense after start of therapy (after 6 months<0.0001). But also the reduction over time is significant (<0.0001). There is a reduction of free lyso-Gb1 after 12 months of treatment in a range of 60% in the mean.

The features of the present invention disclosed in the specification, the claims, the sequence listing and/or the drawings may both separately and in any combination thereof be material for realizing the invention in various forms thereof.

The invention claimed is:

1. A method for generating quantitative data for a subject comprising the steps of:
    a) determining the level of a biomarker in a subject having Gaucher's disease;
    b) determining again the level of the biomarker in a sample from said subject after administration of a therapy to the subject:
    wherein the sample is a blood sample;
    and wherein the biomarker is free lyso-Gb1.

2. The method of claim 1, wherein the therapy is selected from the group consisting of enzyme replacement therapy (ERT), substrate replacement therapy (SRT) and a chaperone based therapy.

3. The method of claim 1, further comprising detecting at least one additional biomarker in the sample from the subject.

4. The method of claim 3, wherein the at least one additional biomarker is selected from the group comprising Chitotriosidase and CCL18.

5. The method of claim 1, wherein the biomarker is detected by means of immunoassay, mass spectrometric analysis, biochip array, functional nucleic acids and/or a fluorescent derivative of free lyso-Gb1.

6. The method of claim 1, wherein the biomarker is detected by means of mass spectrometric analysis.

7. The method of claim 1, wherein a dosage of the therapy is to be increased if the level of the biomarker in the sample as determined in step b) is higher than the level of the biomarker in the sample as determined in step a).

8. The method claim 1, wherein the sample is blood on a dry blood filter card.

\* \* \* \* \*